US008304398B2

(12) United States Patent
't Hoen et al.

(10) Patent No.: US 8,304,398 B2
(45) Date of Patent: Nov. 6, 2012

(54) THERAPEUTIC INTERVENTION IN A GENETIC DISEASE IN AN INDIVIDUAL BY MODIFYING EXPRESSION OF AN ABERRANTLY OR ABNORMALLY EXPRESSED GENE

(75) Inventors: Peter Abraham Christiaan 't Hoen, Leiden (NL); Petronella Johanna Elisabeth Sterrenburg, Voorhout (NL); Johannes Theodorus den Dunnen, Rotterdam (NL); Garrit Jan Boudewijn van Ommen, Amsterdam (NL)

(73) Assignee: Academisch Ziekenhuis Leiden, Leiden (NL)

( * ) Notice: Subject to any disclaimer, the term of this patent is extended or adjusted under 35 U.S.C. 154(b) by 0 days.

(21) Appl. No.: 12/297,251

(22) PCT Filed: Apr. 20, 2007

(86) PCT No.: PCT/NL2007/050175
§ 371 (c)(1),
(2), (4) Date: Nov. 25, 2009

(87) PCT Pub. No.: WO2007/123402
PCT Pub. Date: Nov. 1, 2007

(65) Prior Publication Data
US 2010/0125099 A1    May 20, 2010

(30) Foreign Application Priority Data
Apr. 20, 2006   (WO) ............... PCT/NL2006/000207

(51) Int. Cl.
*A61K 31/70* (2006.01)
*C07H 21/04* (2006.01)
(52) U.S. Cl. ........................................ 514/44; 536/24.5
(58) Field of Classification Search .................. None
See application file for complete search history.

(56) References Cited

U.S. PATENT DOCUMENTS

| | | | |
|---|---|---|---|
| 5,034,506 A | 7/1991 | Summerton et al. | |
| 5,418,139 A | 5/1995 | Campbell | |
| 5,541,308 A | 7/1996 | Hogan et al. | |
| 5,593,974 A | 1/1997 | Rosenberg et al. | |
| 5,608,046 A | 3/1997 | Cook et al. | |
| 5,627,263 A | 5/1997 | Ruoslahti et al. | |
| 5,658,764 A | 8/1997 | Pergolizzi et al. | |
| 5,741,645 A | 4/1998 | Orr et al. | |
| 5,766,847 A | 6/1998 | Jackle et al. | |
| 5,853,995 A | 12/1998 | Lee | |
| 5,869,252 A | 2/1999 | Bouma et al. | |
| 5,962,332 A | 10/1999 | Singer et al. | |
| 5,968,909 A | 10/1999 | Agrawal et al. | |
| 6,124,100 A | 9/2000 | Jin | |
| 6,130,207 A | 10/2000 | Dean et al. | |
| 6,133,031 A | 10/2000 | Monia et al. | |
| 6,172,216 B1 | 1/2001 | Bennett et al. | |
| 6,251,589 B1 | 6/2001 | Tsuji et al. | |
| 6,280,938 B1 | 8/2001 | Ranum et al. | |
| 6,300,060 B1 | 10/2001 | Kantoff et al. | |
| 6,322,978 B1 | 11/2001 | Kahn et al. | |
| 6,329,501 B1 | 12/2001 | Smith et al. | |
| 6,355,481 B1 | 3/2002 | Li et al. | |
| 6,355,690 B1 | 3/2002 | Tsuji | |
| 6,369,038 B1 | 4/2002 | Blumenfeld et al. | |
| 6,379,698 B1 | 4/2002 | Leamon | |
| 6,399,575 B1 | 6/2002 | Smith et al. | |
| 6,514,755 B1 | 2/2003 | Ranum et al. | |
| 6,623,927 B1 | 9/2003 | Brahmachari et al. | |
| 6,653,466 B2 | 11/2003 | Matsuo | |
| 6,653,467 B1 | 11/2003 | Matsuo et al. | |
| 6,670,461 B1 | 12/2003 | Nielsen et al. | |
| 6,794,192 B2 | 9/2004 | Parums et al. | |
| 6,902,896 B2 | 6/2005 | Ranum et al. | |
| 6,982,150 B2 | 1/2006 | Sheetz et al. | |
| 2001/0056077 A1 | 12/2001 | Matsuo | |
| 2002/0049173 A1 | 4/2002 | Bennett et al. | |
| 2002/0055481 A1 | 5/2002 | Matsuo et al. | |
| 2002/0115824 A1 | 8/2002 | Engler et al. | |
| 2002/0165150 A1* | 11/2002 | Ben-Sasson | ............ 514/12 |
| 2003/0073215 A1 | 4/2003 | Baker et al. | |
| 2003/0082763 A1 | 5/2003 | Baker et al. | |
| 2003/0082766 A1 | 5/2003 | Baker et al. | |
| 2003/0109476 A1 | 6/2003 | Kmiec et al. | |
| 2003/0124523 A1* | 7/2003 | Asselbergs et al. | ............ 435/6 |
| 2003/0134790 A1* | 7/2003 | Langenfeld | ............ 514/12 |
| 2003/0235845 A1 | 12/2003 | van Ommen et al. | |

(Continued)

FOREIGN PATENT DOCUMENTS

CA    2319149    10/2001
(Continued)

OTHER PUBLICATIONS

Fainsod et al. Mechanisms of Development 1997, vol. 63, pp. 39-50.*
Wilton et al., "Antisense oligonucleotides, exon skipping and the dystrophin gene transcript," *Acta Myologica XXIV*:222-229 (2005).
Kerr et al., "Bmp Regulates Skeletal Myogenesis at Two Steps," *Molecular & Cellular Proteomics* 2.9:976. 123.8(2003) (Abstract Only).
Kunihiro Tsuchida, "Peptides, Proteins & Antisense: the role of myostatin and bone morphogenetic proteins in muscular disorders," *Expert Opinion of Biologica Therapy*, 6(2):147-153 (2006).

(Continued)

*Primary Examiner* — Tracy Vivlemore
(74) *Attorney, Agent, or Firm* — Edwards Wildman Palmer LLP; Kathleen Williams; Elizabeth Spar

(57) ABSTRACT

The present invention provides means and methods for alleviating genetic disease. A genetic defect that has a phenotype in differentiated cells can lead to defects in precursor cells thereof. These so-called secondary defects contribute to the overall disease of the individual. In the present invention, genetic intervention with the aim to alleviate symptoms of genetic disease is directed toward the primary genetic defect in the differentiated cell and the secondary defect in the precursor cell.

17 Claims, 8 Drawing Sheets

U.S. PATENT DOCUMENTS

| | | | |
|---|---|---|---|
| 2004/0101852 A1 | 5/2004 | Bennett et al. |
| 2004/0132684 A1 | 7/2004 | Sampath et al. |
| 2004/0226056 A1 | 11/2004 | Roch et al. |
| 2005/0096284 A1 | 5/2005 | McSwiggen |
| 2005/0222009 A1 | 10/2005 | Lamensdorf et al. |
| 2005/0246794 A1 | 11/2005 | Khvorova et al. |
| 2005/0277133 A1 | 12/2005 | McSwiggen |
| 2006/0074034 A1 | 4/2006 | Collins et al. |

FOREIGN PATENT DOCUMENTS

| | | | |
|---|---|---|---|
| CA | 2526893 A1 | 11/2004 |
| EP | 438512 A1 | 7/1991 |
| EP | 558697 | 9/1993 |
| EP | 614977 A2 | 9/1994 |
| EP | 850300 | 7/1998 |
| EP | 1054058 | 5/2000 |
| EP | 1015628 A1 | 7/2000 |
| EP | 1133993 | 9/2001 |
| EP | 1160318 | 12/2001 |
| EP | 1191097 | 3/2002 |
| EP | 1191098 | 3/2002 |
| EP | 1 380 644 A1 | 1/2004 |
| EP | 1 487 493 A2 | 12/2004 |
| EP | 1495769 | 1/2005 |
| EP | 1501931 | 2/2005 |
| EP | 1544297 | 6/2005 |
| EP | 1567667 A1 | 8/2005 |
| EP | 1568769 | 8/2005 |
| EP | 1619249 | 1/2006 |
| KR | 2003-0035047 | 5/2003 |
| WO | WO-9301286 A2 | 1/1993 |
| WO | WO-9516718 A1 | 6/1995 |
| WO | WO-9530774 | 11/1995 |
| WO | WO-9712899 | 4/1997 |
| WO | WO-9730067 | 8/1997 |
| WO | WO-9818920 A1 | 5/1998 |
| WO | WO-9849345 A1 | 11/1998 |
| WO | WO-0179283 A1 | 10/2001 |
| WO | WO-0183695 | 11/2001 |
| WO | WO-0202406 | 1/2002 |
| WO | WO-0224906 | 3/2002 |
| WO | WO-0226812 A1 | 4/2002 |
| WO | WO-0229056 | 4/2002 |
| WO | WO-03002739 | 1/2003 |
| WO | WO-03/14145 A2 | 2/2003 |
| WO | WO-03013437 | 2/2003 |
| WO | WO-03037172 | 5/2003 |
| WO | WO-03095647 | 11/2003 |
| WO | WO-2004/11060 A2 | 2/2004 |
| WO | WO-2004015106 | 2/2004 |
| WO | WO-2004016787 | 2/2004 |
| WO | WO-2004048570 | 6/2004 |
| WO | WO-2004083432 | 9/2004 |
| WO | WO-2004083446 | 9/2004 |
| WO | WO-2004101787 | 11/2004 |
| WO | WO2004/108157 A2 | 12/2004 |
| WO | WO-2004108157 A2 | 12/2004 |
| WO | WO-200519453 A2 | 3/2005 |
| WO | WO-2005035550 | 4/2005 |
| WO | WO-200585476 A1 | 9/2005 |
| WO | WO-2005086768 | 9/2005 |
| WO | WO-2005105995 A2 | 11/2005 |
| WO | WO2005/115439 A2 | 12/2005 |
| WO | WO-2005116204 A1 | 12/2005 |
| WO | WO-2006000057 | 1/2006 |
| WO | WO-2006007910 | 1/2006 |
| WO | WO-2006017522 | 2/2006 |
| WO | WO-2006031267 A2 | 3/2006 |

OTHER PUBLICATIONS

Patel et al., "The function of Myostatin and strategies of Myostatin blockade-new hope for therapies aimed at promoting growth of skeletal muscle," *Neuromuscular Disorders* 15(2):117-126 (2005).

Dahlqvist et al., "Functional notch signaling is required for BMP4-induced inhibition of myogenic differentiation," *Development* 130:6089-6099 (2003).

Sterrenburg et al., Gene expression profiling highlights defective myogenesis in DMD patients and a possible role for bone morphogenetic protein 4, *Neurobiology of Disease* 23(1):228-236 (2006).

Iezzi et al., "Deacetylase inhibitors increase muscle cell size by promoting myoblast recruitment and fusion through induction of follistatin," *Developmental Cell* 6:673-684 (2004).

Yokota, et al., Efficacy of Systemic Morpholino Exon-Skipping in Duchenne Dystrophy Dogs, Ann Neurol., 2009, pp. 667-676, vol. 65.

Hansen, Product Development—Addition by subtraction, BioCentury, The Bernstein Report on BioBusiness, Jan. 7, 2008, p. A28 of 38.

Grady, Early drug test shows promise in treating muscular dystrophy, International Herald Tribune, Jan. 3, 2008, Health & Science, p. 9.

Grady, Promising Dystrophy Drug Clears Early Test, The New York Times, Dec. 27, 2007.

Van Deutekom, et al., Local Dystrophin Restoration with Antisense Oligonucleotide PRO051, N. England J. Med., Dec. 27, 2007, pp. 2677-2686.

Van Vliet, et al., "Assessment of the feasibility of exon 45-55 multiexon skipping for duchenne muscular dystrophy." BMC Medical Genetics, Dec. 2008, vol. 9:105 (7 pages).

Verreault, et al. "GENE silencing in the development of personalized cancer treatment: the targets, the agents and the delivery sytems." Curr. Gene Therapy, 2006, vol. 6, pp. 505-553.

McClorey et al., "Induced dystrophin exon skipping in human muscle explants." Neuromuscular Disorders, 16(9-10): 583-90, 2006.

Zhou et al., Current understanding of dystrophin-related muscular dystrophy and therapeutic challenges ahead. Chinese Medical J., Aug. 2006, vol. 119(16): 1381-1391.

Rolland et al., Overactivity of exercise-sensitive cation channels and their impaired modulation by IGF-1 in mdx native muscle fibers: beneficial effect of pentoxifylline. Dec. 2006; Epub Sep. 28, Neurobiology Disease, vol. 24(3): 466-474.

Arruda V R, The role of immunosuppression in gene and cell based treatments for Duchenne Muscular Dystrophy. Molecular Therapy, Jun. 2007, vol. 15(6): 1040-1041.

Matsuo, et al., Exon Skipping during Splicing of Dystrophin mRNA Precursor due to an Intraexon Deletion in the Dystrophin Gene of Duchenne Muscular Dystrophe Kobe. *J. Clin. Invest.* 87, 2127-2131. 1991.

Barany "The ligase chain reaction in a PCR world." PCR Methods Appl. Aug. 1991;1(1):5-16.

Fu, et al., "An Unstable Triplet Repeat in a Gene Related to Myotonic Muscular Dystrophy", *Science*, vol. 255, 1256-1258. 1992.

Reitter B. "Deflazacort vs. prednisone in Duchenne muscular dystrophy: trends of an ongoing study." Brain Dev. 1995;17 Suppl:39-43.

Galderisi, et al., "Myotonic dystrophy: antisense oligonucleotide inhibition of DMPK gene expression in vitro." *Biochem Biophys Res Commun* 221:750-754 (1996).

Denny et al., "Oligo-riboprobes. Tools for in situ hybridisation". Histochemistry (1988) 89:481-493.

Yen, et al., "Sequence-specific cleavage of Huntingtin MRNA by catalytic DNA," *Animals of Neurology*, 1999, pp. 366-373, vol. 46, No. 3.

Austin, et al., "Expression and synthesis of alternatively spliced variants of Dp71 in adult human brain." *Neuromuscular Disorders.* 10(2000) 187-193.

Wang et al. "Adeno-associated virus vector carrying human minidystrophin genes effectively ameliorates muscular dystrophy in mdx mouse model", Dec. 5, 2000, P.N.A.S. 97(25):13714-13719.

Ito, et al., "Purine-Rich Exon Sequences Are Not Necessarily Splicing Enhancer Sequence in the Dystrophin Gene." Kobe J. Med. Sci. 47, 193/202, Oct. 2001.

Caplen, et al., "Rescue of polyglutamine-mediated cytotoxicity by double-stranded RNA-mediated RNA interference," Human molecular genetics, 2002, pp. 175-184, vol. 11, No. 2.

Liu, et al., "Specific inhibition of Huntington's disease gene expression by siRNAs in cultured cells", Proc. Japan Acad. 79, Ser. B (2003), 293-298.

Vickers, et al., "Efficient reduction of target RNAs by small interfering RNA and RNase H-dependent antisense agents. A comparative analysis." *J Biol. Chem.* 278(9):7108-7118 (2003).

Smith et al., "Muscle-specific peptide #5", Mar. 23, 1999. From http://www.ebi.ac.uk/cgi-bin/epo/epofetch?AAW89659, downloaded Jul. 16, 2007. XP 002442550.

Furling. et al., "Viral vector producing antisense RNA restores myotonic dystrophy myoblast functions", Gene Therapy (2003) 10, 795-802.

Langlois, et al., "Hammerhead ribozyme-mediated destruction of nuclear foci in myotonic dystrophy myoblasts," Molecular therapy, 2003, pp. 670-680, vol. 7, No. 5.

Politano et al., "Gentamicin administration in Duchenne patients with Premature stop codon. Preliminary results." Acta Myologica 22:15-21, 2003.

Hasholt, et al., "Antisense downregulation of mutant huntingtin in a cell model," Journal of Gene Medicine, 2003, pp. 528-538, vol. 5, No. 6.

Handa, et al., "The AUUCU repeats responsible for spinocerebellar ataxia type 10 form unusual RNA hairpins." Journal of Biological Chemistry 280(32):29340-29345 (2005).

Alter et al., "Systemic delivery of morpholino oligonucleotide restores dystrophin expression bodywide and improves dystrophic pathology." Nature Medicine. Feb 2006;12(2):175-7. Epub Jan. 29, 2006.

Takeshima et al "Intravenous Infusion of an Antisense Oligonucleotide Results in Exon Skipping in Muscle Dystrophin mRNA of Duchenne Muscular Dystrophy." Pediatric Research. May 2006, 59, 5, p. 690-694.

Burnett, et al., "DNA sequence-specific polyamides alleviate transcription inhibition associated with long GAA. TTC repeats in Friedreich's ataxia," PNAS, 2006, pp. 11497-11502, vol. 103, No. 31.

International Search Report for PCT/NL2009/050006 dated Jul. 31, 2009.

International Search Report for PCT/NL2009/050113 dated Jun. 30, 2010.

Aartsma-Rus, et al., Exploring the Frontiers of Therapeutic Exon Skipping for Duchenne Muscular Dystrophy by Double Targeting within One or Multiple Exons, Molecular Therapy, 2006, pp. 1-7. (Sep. 2006).

Aartsma-Rus et al. Therapeutic Modulation of DMD splicing by Blocking Exonic Splicing Enhancer Sites with Antisense Oligonucleotides Ann NY Acad Sci 2006 pp. 74-76 vol. 1082 (Oct 2006).

Radley et al., Duchenne muscular dystrophy: Focus on pharmaceutical and nutritional interventions. International J. of Biochem. and Cell Biol., vol. 39(3):469-477, Oct. 2006.

Aartsma-Rus et al. Antisense Mediated exon skipping; A Versatile Tool with Therapeutic and Research Applications RNA 2007 pp. 1609-1624 vol. 13 No. 10.

Aartsma-Rus et al. Antisense-Induced Exon Skipping for Duplications in Duchenne Muscular Dystrophy 2007 BMC Med. Genet. 8:43.

Arechavala-Gomeza et al. "Comparative Analysis of Antisense Oligonucleotide Sequences for Targeted Skipping of Exon 51 During Dystrophin pre-mRNA Splicing in Human Muscle" Hum Gene Ther 2007 pp. 798-810 vol. 18 No. 9.

Muntoni, et al., 149th ENMC International Workshop and 1st Treat-NMD Workshop on: "Planning Phase I/II Clinical trials using Systemically Delivered Antisense Oligonucleotides in Duchenne Muscular Dystrophy," Neuromuscular Disorders, 2008, pp. 268-275, vol. 18.

Van Ommen (2008) The Therapeutic Potential of Antisense-Mediated Exon-Skipping Curr Opin Mol. Ther vol. 10(2) pp. 140-149.

Kinali et al. 2009 Local Restoration of Dystrophin Expression With the Morpholino Oligomer AVI-4658 in Duchenne Muscular Dystrophy: A Single-blind, Placebo-Controlled Dose-Escalation, Proof-of Concept Study. Lancet Neurol. vol. 8(10) pp. 918-928.

Popplewell et al. 2009 Design of Phosphorodiamidate Morpholino Oligomers (PMOs) for the Induction of Exon Skipping of the Human DMD Gene Mol. Ther vol. 17(3) pp. 554-561.

Spitali et al. 2009 Exon skipping mediated dystrophin reading frame restoration for small mutations Hum Mut vol. 30(11) pp. 1527-1534.

Aartsma-Rus et al. "Theoretic Applicability of Antisense-Mediated Exon Skipping for Duchenne Muscular Dystrophy" Human Mutation 2009 pp. 293-299 vol. 30 No. 3.

Nakamura et al. 2009 Exon Skipping Therapy for Duchenne Muscular Dystrophy Neuropathology vol. 29(4) pp. 494-501.

Heemskerk et al. 2010 Preclinical PK and PD Studies on 2' O-methyl-phosphorothioate RNA antisense Oligonucleotides in the MDX Mouse Model Mol. Ther vol. 18(6) pp. 1210-1217.

Heemskerk et al. 2009 Development of Antisense-Mediated Exon Skipping as a Treatment for Duchenne Muscular Dystrophy Ann NY Acad Sci vol. 1175 pp. 71-79.

Aartsma-Rus et al. "Guidelines for Antisense Oligonucleotide Design and Insight into Splice-modulation Mechanisms." Molecular Therapy 2009 pp. 548-553 (Published Online Sep. 23, 2008).

Buck et al., "Design Strategies and Performance of Custom DNA Sequencing Primers" Biotechniques. 27:528-536, 1999.

Duboc et al., "Effect of Perindopril on the Onset and Progression of Left Ventricular Dysfunction in Duchenne Muscular Dystrophy." Journal of Amer. Coll. Cardiology, 45(6):855-7, Mar. 15, 2005.

GenBank accession No. AZ993191.1, 2MO278E12F mouse 10kb plasmid UUGC2M library Mus muscu genomic clone UUGC2MO278E12F, genomic survey sequence, entry created on Apr. 27, 2001.

GenBank accession No. EW162121.1, rfat0126_k17.y1 fat Sus scrofa cDNA5-, mRNA sequence, entry created on Aug. 13, 2007, last updated on Mar. 3, 2011.

Hoffman, et al.,"Somatic reversion/suppression of the mouse mdx phenotype in vivo." J. of the Neurological Sciences, 1990, 99: 9-25.

Ikezawa et al. "Dystrophin gene analysis on 130 patients with Duchenne Muscular dystrophy with a special reference to muscle mRNA analysis." Brain & Develop. 20:165-168, 1998.

International Preliminary Report on Patentability and Written Opinion for PCT/EP2007/054842, mailed Nov. 21, 2008.

International Search Report for PCT/EP2007/054842, mailed on Aug. 21, 2007, 3 pages.

O'Shaughnessy et al., "Superior Survival With Capecitabine Plus Docetaxel Combination Therapy in Anthracycline-Pretreated Patients With Advanced Breast Cancer: Phase III Trial Results." Journal of Clinical Oncology, vol. 20, No. 12 (Jun. 15), 2002: pp. 2812-2823.

Rosen et al., "Combination Chemotherapy and Radiation Therapy in the Treatment of Metastatic Osteogenic Sarcoma." Cancer 35: 622-630, 1975.

Verhaart et al., "Prednisolone treatment does not interfere with 2OmePS antisense-mediated exon skipping in DMD." Human Gene Therapy. Mar. 2012, 23(3): 262-273. doi:10.1089/hum.2011.127.

Aartsma-Rus, et al., "Functional Analysis of 114 Exon-Internal AONs for Targeted DMD Exon Indication for Steric Hindrance of SR Protein Binding Sites," Oligonucleotides, 2005, pp. 284-297, vol. 15.

Aartsma-Rus, et al., Antisense-Induced Multiexon Skipping for Duchenne Muscular Dystrophy Makes More Sense, Am. J. Hum. Genet, 2004 pp. 83-92, vol. 74.

Aartsma-Rus, et al., Targeted exon skipping as a potential gene correction therapy for Duchenne muscular dystrophy, Neuromuscular Disorders, 2002, S71-S77, vol. 12.

Aartsma-Rus, et al., Therapeutic antisense-induced exon skipping in cultured muscle cells from six different patients, Human Molecular Genetics, 2003, pp. 907-914, vol. 12, No. 8.

Abbs et al., A convenient multiplex PCR system for the detection of dystrophin gene deletions: a comparative analysis with cDNA hybridisation shows mistypings by both methods, J. Med. Genet, 1991, pp. 304-311, vol. 28.

Agrawal and Kandimalla, et al., "Antisense therapeutics: is it as simple as complementary base recognition?" Mol. Med. Today, Feb. 2000, vol. 6., pp. 72-81.

Anderson et al., Correlated NOS-I[mu] and myf5 expression by satellite cells in mdx mouse muscle regeneration during NOS manipulation and deflazacort treatment. Neuromusccular Disorders, Jun. 2003, vol. 13(5): 388-396.

Arzumanov, et al.,"Inhibition of HIV-1 Tat-dependent trans activation by steric block chimeric 2'-O-methyl/LNA oligoribonucleotides." Biochemistry, 2001, vol. 40, pp. 14645-14654.

Austin et al. "Cloning and characterization of alternatively spliced isoforms of Dp71." *Hum Mol Genetics* 1995 vol. 4 No. 9 1475-1483.
Australian Office Action for AU 2009240879, dated Jun. 22, 2011.
Barabino et al. (1992) "Antisense probes targeted to an internal domain in US snRNP specifically inhibit the second step of pre-mRNA splicing" Nucleic Acids Res. 20(17):4457-4464.
Bionity.Com NEWS-Center, Leiden University Medical Center and Prosensa B.V. Announce First Successful Clinical Study with RNA-based Therapeutic PRO051, dated Jan. 3, 2008, <http://www.bionity.com/news/e/76185>.
Biopharmaceutiques, Merging Pharma & Biotech, Edition 48, Jan. 10, 2008. <http://www.biopharmaceutiques.com/en/num>, visited Jan. 11, 2008.
Bremmer-Bout, et al., Targeted exon skipping in transgenic hDMD mice: A model for direct preclinical screening of human-specific antisense oligonucleotides. Mol Ther. Aug. 2004; 10(2):232-40.
Brett et al., EST comparison indicates 38% of human m RNAs contain possible alternative splice forms. FEBS Lett 474(1): 83-86, 2000.
Brown, et al., "Structure and mutation of the dystrophin gene" in Dystrophin: Gene, protein and cell biology (Brown and Lucy, eds) Cambridge University Press, Cambridge, 1997, p. 1-16.
Canadian Office Action for CA 2,524,255, dated Jul. 6, 2011.
Cartegni, et al., Abstract, Listening to silence and understanding nonsense: exonic mutations that affect splicing, Nature Reviews Genetics, Apr. 2002, pp. 285-298, vol. 3.
Chaubourt et al., Muscular nitric oxide synthase ([mu]NOS) and utrophin. J. of Physiology Paris, Jan.-Mar. 2002 ; vol. 96(1-2): 43-52.
Coulter et al. Identification of a new class of exonic splicing enhancers by in vivo selection. Mol. Cell. Biol. 17(4) 2143-50 (1997).
Crooke. in Basic Principles of Antisense Therapeutics, Springer-Verlag, Eds, New York, 1998, pp. 1-50.
De Angelis et al., Chimeric snRNA molecules carrying antisense sequences against the splice junctions of exon 51 of the dystrophin pre-mRNA exon skipping and restoration of a dystrophin synthesis in delta 48-50 DMD cells, PNAS, Jul. 9, 2002, vol. 99, No. 14. p. 9456-9461.
Declaration of Dr. Adrian Krainer (submitted in Third Party's Stmt for JP Appl. No. 2002-529499, dated Oct. 29, 2010).
Dickson, et al., Screening for antisense modulation of dystrophin pre-mRNA splicing, Neuromuscular Disorders, Oct. 2002, pp. S67-S70, vol. 12., Suppl. 1.
Dirkson, et al., Mapping the SF2/ASF Binding Sites in the Bovine Growth Hormone Exonic Splicing Enhancer, The Journal of Biological Chemistry, Sep. 15, 2000, pp. 29170-29177, vol. 275, No. 37.
Dunckley, et al., Modification of splicing in the Dsytrophin gene in cultured Mdx muscle cells by antisense oligoribonucleotides. Hum Mol Genet. 1995 7(7):1083-90.
Dunckley, et al., Modulation of Splicing in the DMD Gene by Antisense Oligoribonucleotides, Nucleosides & Nucleotides, 1997, pp. 1665-1668, vol. 16, No. 7-9.
Erba et al., Structure, chromosome location, and expression of the human gamma-actin gene: differential evolution, location, and expression of the cytoskeletal beta- and gamma-actin genes. Mol. Cell. Biology, 1988, 8(4):1775-89.
Errington, et al., Target selection for antisense oligonucleotide induced exon skipping in the dystrophin gene. J Gene Med. Jun. 2003; 5(6):518-27.
European Patent Office Action dated Jan. 29, 2007.
Feener et al., Alternative splicing of human dystrophin mRNA generates isoforms at the carboxy terminus. Nature, 338 (6215): 509-511 (1989).
Fluiter, K., "In Vivo tumor growth inhibition and biodistribution studies of locked nucleic acid (LNA) antisense oligonucleotides," Nucl. Acids Research 2003, vol. 31., No. 3., pp. 953-962.
Genes VII, Jan. 2000, Benjamin Lewin, Chapter 22, Nuclear Splicing, pp. 704-705.
Ginjaar, et al., Dystrophin nonsense mutation induces different levels of exon 29 skipping and leads to variable phenotypes within one BMD family, European Journal of Human Genetics (2000) 8, 793-796.
Granchelli et al., Pre-clinical screening of drugs using the mdx mouse. Neuromuscular Disorders, Pergamon Pres. vol. 10(4-5): 235-239, Jun. 2000.
Gryaznov, "Oligonucleotide N3' → P5' phosphoramidates as potential therapeutic agents." Biochemistry et Biophys. Acta, 1999, vol. 1489, pp. 131-140/.
Hagiwara, et al. "A novel point mutation (G-1 to T) in a 5' splice donor site of intron 13 of the dystrophin gene results in exon skipping and is responsible for Becker muscular dystrophy." Am J. Hum Genet. Jan. 1994 ;54(1):53-61.
"Hope for muscular dystrophy drug", *The Daily Telegraph*, Dec. 28, 2007.
Hussey, et al., Analysis of five Duchenne muscular dystrophy exons and gender determination using conventional duplex polymerase chain reaction on single cells, Molecular Human Reproduction, 1999, pp. 1089-1094, vol. 5, No. 11.
International Preliminary Examination Report, International Application No. PCT/NL01/00697, dated Aug. 1, 2002.
International Search Report, International Application No. PCT/NL 2008/050470, dated Jul. 2, 2009.
International Search Report, International Application No. PCT/NL 2008/050475, dated Jun. 25, 2009.
International Search Report, International Application No. PCT/NL 2008/050673, dated Feb. 9, 2009.
International Search Report, International Application No. PCT/NL01/00697, dated Dec. 21, 2001 (2 pages).
International Search Report, International Application No. PCT/NL2004/000196, Oct. 28, 2004 (8 pages).
International Search Report, International Application No. PCT/NL2006/000209, dated Oct. 5, 2006.
Karras, et al., Deletion of Individual Exons and Induction of Soluble Murine Interleukin-5 Receptor-alpha Chain Expression through Antisense Oligonucleotide-Mediated Redirection of Pre-mRNA Splicing, Molecular Pharmacology, 2000, pp. 380-387, vol. 58.
Kurrek, et al., "Design of antisense oligonucleotides stabilized by locked nucleic acids." Nucleic Acids Research, 2002, vol. 30, No. 9, pp. 1911-1918.
Laptev et al., (1994) "Specific inhibition of expression of a human collagen gene (COL1A1) with modified antisense oligonucleotides. The most effective target sites are clustered in double-stranded regions of the predicted secondary structure for the mRNA" Biochemistry 33(36):11033-11039.
Lee et al., Receptor mediated uptake of peptides that bind the human transferin receptor. Eur. J. Biochem. 268, 2004-2012 (2001).
Leiden University Medical Center and Prosensa B.V. Announce New England Journal of Medicine Publication of First Successful Clinical Study with RNA-based Therapeutic PRO051 in Duchenne Muscular Dystrophy, Dec. 27, 2007.
Letter from Katholieke Universiteit Leuven to Dr. N. Goemans, Child Neurology, UZ dated Jan. 22, 2008, regarding a Phase I/II, open label, escalating dose, pilot study to assess the effect, safety, tolerability and pharmacokinetics of multiple subcutaneous doses of PRO051 in patients with Duchenne muscular dystrophy. PRO051-02 (translation provided).
Letter from Prosensa Therapeutics B.V. to Federal Agency for Medicines and Health Products dated Jan. 9, 2008, regarding a Phase I/II, open label, escalating dose, pilot study to assess the effect, safety, tolerability and pharmacokinetics of multiple subcutaneous doses of PRO051 in patients with Duchenne muscular dystrophy.
Liu et al., "A mechanism for exon skipping caused by nonsense or missense mutations in BRCA1 and other genes." Nat Genet. Jan. 2001;27(1):55-8.
Liu, et al., Identification of functional exonic splicing enhancer motifs recognized by individual SR proteins, Genes & Development, 1998, pp. 1998-2012, vol. 12.
Lu et al., "Functional amounts of dystrophin produced by skipping the mutated exon in the *mdx* dystrophic mouse." Nature Medicine, 8: 1009, 2003.
Lu, et al., Massive Idiosyncratic Exon Skipping Corrects the Nonsense Mutation in Dystrophic Mouse Muscle and Produces Functional Revertant Fibers by Clonal Expansion, The Journal Cell Biology, Mar. 6, 2000, pp. 985-995, vol. 148, No. 5.

LUMC and Prosensa report positive results of DMD study, Pharmaceutical Business Review Online, dated Dec. 28, 2007, <http://www.pharmaceutical-business-review.com/article_news_print.asp?guid=8462FD44-F35D-4E0B-BC>.

Mann, et al., Antisense-induced exon skipping and synthesis of dystrophin in the mdx mouse. Proc Natl Acad Sci USA Jan. 2, 2001: 98(1):42-7.

Mann, et al., Improved antisense oligonucleotide induced exon skipping in the mdx mouse model of muscular dystrophy. J Gene Med. Nov.-Dec. 4, 2002(6):644-54.

Matsuo et al. (1992) "Partial deletion of a dystrophin gene leads to exon skipping and to loss of an intra-exon hairpin structure from the predicted mRNA precursor" Biochem. Biophys. Res. Commun. 182(2):495-500.

Matsuo, et al., "Duchenne/Becker muscular dystrophy: from molecular diagnosis to gene therapy." Brain Dev. (1996) 18(3):167-172.

Monaco, et al., An Explanation for the Phenotypic Differences between Patients Bearing Partial Deletions of the DMD Locus, Genomics, 1988, pp. 90-95, vol. 2.

Moon, et. al., "Target site Search and effective inhibition of leukaemic cell growth by a covalently closed multiple anti-sense oligonucleotide to c-myb" The Biochemical Journal, Mar. 1, 2000, vol. 346 Pt 2, pp. 295-303.

Munroe (1988) "Antisense RNA inhibits splicing of pre-mRNA in vitro" EMBO J. 7(8):2523-2532.

Muntoni et al. "A Mutation in the Dystrophin Gene Selectively Affecting Dystrophin Expression in the Heart." *J. Clin Invest*. vol. 96 Aug. 1995. 693-699.

"New Clinical Trial Results Show How Personalized Medicine Will Alter Treatment of Genetic Disorders", Medical News Today, Dec. 29, 2007 <http://www.medicalnewstoday.com/article/92777.php>.

Nishio et al. "Identification of a Novel First Exon in the Human Dystrophin Gene and of a New Promoter Located More Than 500 kb Upstream of the Nearest Known Promoter." *J. Clin. Invest*. vol. 94, Sep. 1994 1037-1042.

Notice of Opposition filed against EP 1 619 249 B, dated Jun. 23, 2009.

Office Action for U.S. Appl. No. 10/395,031 dated Oct. 16, 2009.
Office Action for U.S. Appl. No. 11/233,507, dated Jun. 15, 2007.
Office Action for U.S. Appl. No. 11/233,507, dated Mar. 19, 2008.
Office Action for U.S. Appl. No. 11/233,507, dated May 29, 2009.
Office Action for U.S. Appl. No. 11/982,285, dated Sep. 18, 2009.
Office Action for U.S. Appl. No. 10/395,031, dated Apr. 2, 2009.
Office Action for U.S. Appl. No. 10/395,031, dated Aug. 23, 2007.
Office Action for U.S. Appl. No. 10/395,031, dated Feb. 6, 2006.
Office Action for U.S. Appl. No. 10/395,031, dated Jul. 8, 2005.
Office Action for U.S. Appl. No. 10/395,031, dated May 30, 2008.
Office Action for U.S. Appl. No. 10/395,031, dated Nov. 30, 2006.
Office Action for U.S. Appl. No. 11/233,495, dated Dec. 1, 2008.
Office Action for U.S. Appl. No. 11/233,495, dated Jun. 25, 2009.
Office Action for U.S. Appl. No. 11/233,507, dated Nov. 12, 2008.
Office Action for U.S. Appl. No. 11/982,285, dated May 4, 2009.

Opalinksa and Gerwitz: "Nucleic-acid therapeutics: basic principles and recent applications." Nature Reviews Drug Discovery, Jul. 2002, vol. 1., pp. 503-514.

Oxford Dictionary of English, 2nd Edition, Revised, Oxford University Press, p. 158, 2003.

Patentee's response during prosecution of opposed patent, dated Jul. 28, 2009.

Pramono, et al., Induction of exon skipping of the dystrophin transcript in lymphoblastoid cells by transfecting an antisense oligodeoxynucleotide complementary to an exon recognition sequence. Biochem Biophys Res Commun. Sep. 13, 1996; 226(2):445-9.

Rando, Thomas A., "Oligonucleotide-mediated gene therapy for muscular dystrophies." Neuromuscular Disorders, 2002, vol. 12, pp. S55-S60.

Request for an Opinion under Section 74(A) in relation to Patent No. EP (UK) 1 619 249B in the name of Academisch Ziekenhuis Leiden, opinion issued on Jun. 4, 2009.

Request for UK IPO Opinion (Section 74A & Rule 93)—EP(UK) 1619249 dated Mar. 9, 2009.

Roberts et al., Direct detection of dystrophin gene rearrangements by analysis of dystrophin mRNA in peripheral blood lymphocytes. Am. J. Hum. Genet. 49(2): 298-310 (1991).

Roberts, et al., "Exon structure of the human dystrophin gene." Genomics, 1993, vol. 16, No. 2, pp. 536-538. (1993).

Roberts, et al., Direct diagnosis of carriers of Duchenne and Becker muscular dystrophy by amplification of lymphocyte RNA. Lancet, 336 (8730-8731): 1523-6 (1990).

Roberts, et al., Searching for the 1 in 2,400,000: a review of dystrophin gene point mutations. Hum. Mut. 4:1-11 (1994).

Scanlon "Anti-Genes: siRNA, Ribozymes & Antisense" Curr. Pharm. Botech. 5:415-420, 2004.

Segalat et al., Capon expression in skeletal muscle is regulated by position, repair, NOS activity, and dystrophy. Experimental Cell Research, Jan. 2005, vol. 302(2): 170-179.

Sertic, et al., "Deletion screening of the Duchenne/Becker muscular dystrophy gene in Croatian population" Coll. Antropol. 1997, 1:151-156.

Shapiro and Senapathy, "RNA splice junctions of different classes of eukaryotes: sequence statistics and functional implications in gene expression." Nucleic Acids Research, 1987, vol. 15. No. 17, pp. 7155-7174.

Sherratt, et al., Exon Skipping and Translation in Patients with Frameshift Deletions in the Dystrophin Gene, Am. J. Hum. Genet, 1993, pp. 1007-1015, vol. 53.

Shiga, et al., Disruption of the Splicing Enhancer Sequence within Exon 27 of the Dystrophin Gene by a Nonsense Mutation Induces Partial Skipping of the Exon and Is Responsible for Becker Muscular Dystrophy, J. Clin. Invest., Nov. 1997, pp. 2204-2210, vol. 100, No. 9.

Simoes-Wust, et al., bcl-xL Antisense Treatment Induces Apoptosis in Breast Carcinoma Cells, Int. J. Cancer, 2000, pp. 582-590, vol. 87.

Surono et al. "Six Novel Transcripts that Remove a Huge Intron Ranging from 250 to 800 kb Are Produced by Alternative Splicing of the 5' Region of the Dystrophin Gene in Human Skeletal Muscle." *BBRC* 239 895-899 (1997).

Surono et al., "Chimeric RNA/ethylene-bridged nucleic acids promote dystrophin expression in myocytes of duchenne muscular dystrophy by inducing skipping of the nonsense mutation-encoding exon." Human Gene Therapy, 15:749-757, 2004.

Suter, et al., Double-target antisense U7 snRNAs promote efficient skipping of an aberrant exon in three human B-thalassemic mutations, Human Molecular Genetics, 1999, pp. 2415-2423, vol. 8, No. 13.

Suwanmanee et al. (2002) "Restoration of Human b-globin Gene Expression in Murine and Human IVS2-654 Thalassemic Erythroid Cells by Free Uptake of Antisense Oligonucleotides" Mol. Pharmacology 62(3):545-553.

Takashima et al. Oligonucleotides Against a Splicing Enhancer Sequence Led to Dystrophin Production in Muscle Cells From a Duchenne Muscular Dystrophy Patient Brain Dev Dec. 2001; 23:788-90.

Takeshima, et al., Modulation of In Vitro Splicing of the Upstream Intron by Modifying an Intra-Exon Sequence Which is Deleted from the Dystrophin Gene in Dystrophin Kobe, J. Clin. Invest., Feb. 1995, pp. 515-520, vol. 95.

Tanaka, et al., Polypurine Sequences within a Downstream Exon Function as a Splicing Enhanced, Molecular and Cellular Biology, Feb. 1994, pp. 1347-1354, vol. 14, No. 2.

Thanh, et al., "Characterization of revertant muscle fibers in Duchenne musclar dystrophy, using exon-specific monoclonal antibodies against dystrophin." Am. J. Hum. Genet. 1995, vol. 56, pp. 725-731.

Third Party's Statement for Japan Appl. No. 2002-529499, dated Oct 29, 2010.

Tian H, Kole R, "Selection of novel exon recognition elements from a pool of random sequences." Mol Cell Biol 15(11):6291-8. (1995).

Treat-NMD Neuromuscular Network, Jan. 11, 2008.

Van Deutekom et al. Advances in Duchenne Muscular Dystrophy Gene Therapy 2003 Nat Rev Genet 4(10): 774-83.

Van Deutekom, et al., Antisense-induced exon skipping restores dystrophin expression in DMD patient derived muscle cells, Human Molecular Genetics, 2001, pp. 1547-1554, vol. 10, No. 15.

Watakabe, et al., The role of exon sequences in splice site selection, Genes & Development, 1993, pp. 407-418, vol. 7.

Wells et al. Enhanced in Vivo Delivery of Antisense Oligonucleotide to Restore Dystrophin Expression in Adult MDX Mouse Muscle FEBS Letters 2003 552: 145-149.

Wheway and Roberts. "The Dystrophin Lymphocyte promoter revisited: 4.5-megabase intron, or artifacts?" *Neuromuscular Disorders* 13(2003) 17-20.

Wilton, et al., Specific removal of the nonsense mutation from the mdx dystrophin mRNA using antisense oligonucleotides, Neuromuscular Disorders, 1999, pp. 330-338, vol. 9.

* cited by examiner

SEQUENCE LISTING

<160> NUMBER OF SEQ ID NOS: 11

<210> SEQ ID NO 1
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gcauggcucg cgccuccuag cag                                                23

<210> SEQ ID NO 2
<211> LENGTH: 22
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 2
ccagugcugu ggaucugcuc uu                                            22

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cuuccacauc cgguuguuu                                                19

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgagcctttc cagcaagttt gtt                                           23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atcagcattc ggttaccagg                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggatgctgc tgaggttaaa                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatcatcagc aatgcctcct                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 8
ccatccacag tcttctgggt                                              20

<210> SEQ ID NO 9
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ggccaaaccu cggcuuaccu                                              20

<210> SEQ ID NO 10
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
agacuggagc cgguaa                                                  16

<210> SEQ ID NO 11
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uggcucggcu ggcggg                                                  16
```

THERAPEUTIC INTERVENTION IN A GENETIC DISEASE IN AN INDIVIDUAL BY MODIFYING EXPRESSION OF AN ABERRANTLY OR ABNORMALLY EXPRESSED GENE

This application is the U.S. National Phase of, and Applicants claim priority from, International Application Number PCT/NL2007/050175 filed Apr. 20, 2007 and International Application Number PCT/NL2006/000207 filed Apr. 20, 2006 which are incorporated herein by reference.

BACKGROUND OF THE INVENTION

Incorporation of Sequence Listing

Incorporated herein by reference in its entirety is the Sequence Listing for the application. The Sequence Listing is disclosed on a computer-readable ASCII text file titled, "Sequence_1564-6PCTUS.txt", created on Sep. 29, 2009. The sequence.txt file is 2.34 kb in size.

The invention relates to the field of genetic diseases. Specifically the invention relates to the improvement of a therapy for a genetic disease by correction of a secondary effect of a genetic disease in an individual.

A genetic disease is a disease caused by abnormalities in the genetic material of an individual. The expression of a disease in an individual is not only dependent on genetic factors, environmental factors do also play a role. A possible classification for genetic disorders is a division in two different types, monogenic or polygenic. A monogenic genetic disorder is caused by a mutation that occurs in the DNA sequence of one gene. There are more than 6,000 known monogenic disorders (Human Genome Project Information). Examples are cystic fibrosis, sickle cell anemia, Marfan syndrome, Huntington's disease, and hereditary hemochromatosis. Monogenic diseases are inherited in recognizable patterns: autosomal dominant, autosomal recessive, and X-linked. A polygenic genetic disease is caused by mutations in multiple genes. Two categories that can be distinguished within the group of genetic disorders are chromosomal and mitochondrial disorders.

A chromosomal genetic disease is caused by abnormalities in chromosome structure. Abnormalities in chromosome structure as missing or extra copies or gross breaks and rejoinings (translocations), can result in disease. Some types of major chromosomal abnormalities can be detected by microscopic examination. Down syndrome or trisomy 21 is a common disorder that occurs when a person has three copies of chromosome 21.

A mitochondrial genetic disease is a relatively rare type of genetic disease. This type of disorder is caused by mutations in the nonchromosomal DNA of mitochondria. Each mitochondrion may contain 5 to 10 circular pieces of DNA. A chromosomal as well as a mitochondrial genetic disease can be either a monogenic disease or a polygenic disease.

DESCRIPTION OF THE INVENTION

Identification of a gene in which a mutation has occurred offers an opportunity to develop a specific therapy. Research into the identification of genes, involved in diverse genetic diseases, has been intense for the past decade. The Human Genome Project which has identified practically all genes in human DNA had an important role in the progress of this type of research. Many of the genetic diseases are caused by a defect in crucial gene. Often, the defect results in no or a reduced amount of function of a product of the affected gene. Therapies that utilize the molecular knowledge of the underlying reasons for such genetic defects typically aim to provide the affected cells with a (partially) functional gene product. In the present invention it has been found that other genes than the affected can be deregulated in cells of said individual and that said deregulation can add to the severity and/or symptoms of the disease. Surprisingly, this deregulation (aberrant expression) was found even when the gene affected by the mutation underlying the genetic defect, is not directly responsible for expression of the aberrantly expressed gene or when the aberrant expression of the gene is not directly related to the function of the protein that is affected by the genetic defect. One object of the present invention is therefore to correct at least one of secondary, potentially disease aggravating effect of said genetic defect in said patient by modulating the expression of said aberrantly expressed gene. Thus it appears that besides a mutated gene which can be identified as a causal factor for a genetic disease there are other genes which are aberrantly expressed, although those genes seem not to be directly influenced by said mutated gene or the normal counterpart thereof. The present invention identifies several of said aberrantly expressed genes. The expression of a deregulated gene (aberrantly expressed gene) is different from the normal situation in a healthy individual. Such deregulated expression, aberrant expression is undesired. The present observation was made in genetic diseases that are caused by a defect in differentiated cells. It has been found that genes can be deregulated already in the precursor of said differentiated cell even when the gene affected by the mutation (the cause for the genetic defect) is not normally expressed in said precursor cell. In other words, said aberrantly expressed gene is found in other cells than the differentiated cells which are generally believed to express the phenotype of said genetic disease. The invention offers new insights for the treatment of genetic disease, particular for genetic disease caused by a (partial) lack of function or absence of a gene product in differentiated cells of said individual. In the present invention, expression of said aberrantly expressed gene is modified, either in cultures of precursor cells of said differentiated cells or directly in a patient. When applied in cultures of said precursor cells, it enhances the capacity of said precursor cells to form new differentiated cells after transplantation of said precursor cells to a patient, thereby improving the success of said cell transplantation therapy. When applied directly in the patient, the invention provides a method for alleviating an aggravating symptom of a genetic disease in an individual, wherein said symptom is preferably the reduced capacity of said precursor cells to differentiate into said differentiated cells, wherein said disease is the result of a malfunctioning gene in a differentiated cell of said individual, said method comprising modifying expression of at least one aberrantly expressed gene in said precursor cell, wherein said aberrantly expressed gene is not said malfunctioning gene. The malfunctioning gene and the direct effects caused by its defect are typically referred to as the primary effect, whereas indirect effects that occur subsequently as a result of the malfunctioning of the cell comprising said genetic defect are often referred to as secondary effects. These secondary effects typically are not a direct result of the malfunctioning of the gene.

The invention further provides the use of a compound for modifying expression of at least one gene, for the manufacture of a medicament for alleviating a symptom of a genetic disease in an individual, wherein said disease is the result of a genetic defect in a differentiated cell of said individual, wherein said gene is aberrantly expressed in a precursor of said differentiated cell and wherein said aberrant expression is not directly related to the mutation underlying said genetic defect (the malfunctioning gene).

The genetic defect typically affects at least part of the function of a gene or the product thereof. This can be caused by a great variety of mutations. For instance, a mutation can be in the coding region of the gene thereby resulting in the production of a defective protein/RNA. On the other hand, the mutation can also be in one or more of the regulatory sequence that govern the expression of the gene product. Such a mutation can also result in a loss of (partial) function of a gene product of said gene, as the level of gene product in the cell, or the timing of expression in the cell is changed. The type of mutation can also vary. The mutation can for instance be a deletion, an insertion, an inversion or a point mutation. There are also mutations that are so-called silent mutations, i.e. that do not significantly affect the health of an individual. Examples of such mutations are point mutations in codons that, due to the redundancy in the coding potential, do not change the amino acid that is incorporated into the protein. It will be clear that silent mutations are not within the scope of the present invention. A mutated gene, as a cause of a genetic disease, as used in the invention is a gene with a non-silent mutation.

Cells in the body typically have a limited life span. Many of these cells are replenished by so-called precursor cells. For instance, dead skin cells are continuously replenished from precursor (stem) cells. Cells of the intestinal lining are similarly replenished by so-called stem cells. Muscle cells are typically (re)generated by fusion with precursor cells called myoblasts; blood cells are replenished by precursor cells that ultimately originate in the bone marrow of an individual. Regeneration can only occur when the precursor cell gives up its primitive state in a process called differentiation. Precursor cells themselves can also have a limited life span and/or activity and if so they are replaced by other precursor cells with a more extensive life span and/or regenerative potential. The end cell with limited life span and limited self-renewal potential is referred to as a differentiated cell, whereas the precursor often has a larger potential for self-renewal is called an un-differentiated cell. This latter is often due to the fact that the differentiated cells exhibit functions that are not exhibited by the precursor. In a preferred embodiment, said precursor cell is a myoblast and/or a precursor thereof. In a preferred embodiment said differentiated cell is a muscle cell.

An individual with a genetic disease can exhibit many symptoms. When reference is made to alleviating a symptom of a disease, it is meant that the severity of a symptom is at least reduced. In case of muscular wasting, for example, symptoms of the disease encompass among others, reduction of muscle strength with age, reduction in muscle mass with age, a limited life span and a decrease in the quality of life with age (for instance, the inability to walk, dependency on care and medication). In the example of muscle wasting, alleviating a symptom can be improving muscle strength, life span and/or improving quality of life in general, when compared with an untreated individual with the same prognosis as the treated individual would have had in the absence of treatment.

A gene that is aberrantly expressed in an individual suffering from said genetic disease, can either be expressed too low or too high compared to the same gene that is physiologically expressed in a healthy individual. Modifying expression in a method or use according to the invention, comprises raising expression of said aberrantly expressed gene when expressed lower than said gene in a normal state or lowering expression of said aberrantly expressed gene when expressed higher than said gene in said normal state. Raising expression when expressed too low or lowering expression when expressed too high corrects changes secondary to the primary genetic defect and alleviates a symptom of a genetic disease. In doing so, expression of said aberrantly expressed gene is brought to physiologically more acceptable, more plausible and/or more typical levels. In a preferred embodiment of the invention expression of said aberrantly expressed gene is essentially normalized. Physiologically acceptable, more plausible and/or more typical levels will often be levels that are approximately normal levels. Normal levels are levels that can be found in a healthy individual of the same age and constitution. Physiologically acceptable, more plausible and/or more typical levels can fall outside a normal range but do still provide a sufficient function for an individual. In a preferred embodiment the invention provides a use or a method according to the invention, wherein modifying said expression comprises approximating levels of the normal state.

Modifying expression can be achieved in a number of ways. Lowering expression of an aberrantly expressed gene can for example be realized by applying anti-sense therapy or by administering a repressor protein that binds to the promoter of said aberrantly expressed gene. Raising expression of an aberrantly expressed gene is for instance effected by the addition of a transgene that expresses said aberrantly expressed gene, by the addition and/or activation of a transcription factor that stimulates the expression of said aberrantly expressed gene and/or by activating the promoter and/or enhancer-sequence of said aberrantly expressed gene. In a preferred embodiment of the invention expression is modified by providing said individual with an anti-sense sequence of said aberrantly expressed gene. There are currently many different anti-sense approaches to down-regulate production of a gene product. Anti-sense technology exploits oligonucleotide analogs to bind to target RNAs via Watson-Crick hybridisation. Once bound, the anti-sense agent either disables or induces the degradation of the target RNA. Anti-sense agents can also alter splicing. During the past decade, much has been learned about the basic mechanisms of anti-sense, the medicinal chemistry, and the pharmacologic, pharmacokinetic, and toxicologic properties of anti-sense molecules. Anti-sense technology has proven valuable in gene functionalisation and target validation. With one drug marketed, Vitravene, and approximately 20 anti-sense drugs in clinical development anti-sense drugs are important drugs in the treatment of a wide range of diseases (for review see [1]). Non-limiting examples of some of the newer anti-sense approaches are interference RNA (RNAi), microRNA and splice interference techniques such as exon-skipping. An anti-sense sequence is preferably administered as a single stranded molecule or as part of a hairpin molecule. An anti-sense sequence can be administered directly or be produced in a cell by means of a (virally-transduced) expression cassette.

An anti-sense oligonucleotide is preferably provided to a cell as part of a gene delivery vehicle. Such a vehicle is preferably a liposome or a viral gene delivery vehicle. Liposomes are well known in the art and many variants are available for gene transfer purposes. Various viral gene delivery are currently used to transfer genes into target cells. In the present invention it is preferred to use those viral vectors that do not express their own genes but only the transferred genes. The anti-sense molecule may be present as such in the gene delivery vehicle. In a viral vector, the anti-sense molecule is preferably provided as an expression cassette wherein the expression cassette encodes a transcript comprising said anti-sense oligonucleotide. A preferred viral delivery vehicle is an adenoviral vector and more preferably an adeno-associated virus vector. The invention thus also provides such expression cassettes, vectors and gene delivery vehicles. It is within the skill of the artisan to design suitable transcripts. Preferred for the invention are PolIII driven transcripts. Preferably in the form of a fusion transcript with an U1 or U7 transcript. Such fusions may be generated as described in references [2-4]. In the present invention an oligonucleotide is a polymer of DNA or RNA nucleotides (typically between 5 and 300 nucleotides). Oligonucleotides can be synthesized in vitro or in vivo. In the latter context they are sometimes also referred to an anti-sense molecule/sequence, siRNA, miRNA and the like.

In a preferred embodiment an oligonucleotide comprises between 5-300 nucleotides, more preferably between 15-100 nucleotides, more preferably between 15-40 nucleotides and more preferably between 15 and 25 nucleotides. Said lengths are preferred for the region of complementarity of said oligonucleotide or functional equivalent thereof. An oligonucleotide or functional equivalent thereof, of between 15 and 40 nucleotides can have one or two mismatches with the region said oligonucleotide or functional equivalent is complementary to. In case of said one or two mismatches the region of complementarity preferably comprises a continuous stretch of at least 15 nucleotides. I.e. an oligonucleotide or functional equivalent thereof complementary to any stretch of 15 can have one or two mismatches. Preferably said oligonucleotide or functional equivalent thereof has one or more preferably no mismatches with the region it is complementary to. If the oligonucleotide has more than 15 nucleotides it may have up to 15% mismatches. If the calculated number of mismatches based on the percentage rule is a number between two integers, the maximum allowed number of mismatches is the higher integer number. For example, an oligonucleotide having a continuous stretch of 16 nucleotides complementarity can have $16*0.15=2.4$ nucleotide mismatches. Thus the maximum number of mismatches allowed in this oligonucleotide is 3. In a preferred embodiment, the generated oligonucleotide is complementary to a consecutive part of between 15 and 50 nucleotides and more preferred said oligonucleotide comprises RNA and even more preferred said oligonucleotide is 2'-O-methyl RNA and has a full-length phosphorothioate backbone. 2'0-methyl RNA is a nucleic acid analogue that is characterized by good hybridization properties that it imparts with complimentary DNA or RNA as well as, an increased stability against enzymatic degradation compared to natural nucleic acids. Most antisense oligonucleotides currently in clinical development incorporate phosphorothioate backbone modifications, to promote resistance to nucleases while preserving the ability to stimulate cleavage of the mRNA target by ribonuclease (RNase) H. The complementary oligonucleotide is preferably complementary to a consecutive part of between 13 and 50 nucleotides of said exon RNA. In another embodiment the complementary oligonucleotide is complementary to a consecutive part of between 16 and 50 nucleotides of said exon RNA. Preferably, the oligonucleotide is complementary to a consecutive part of between 13-25 nucleotides of said exon RNA. Preferably between 14 and 25 nucleotides of said exon RNA. Different types of nucleic acid may be used to generate the oligonucleotide. Preferably, the oligonucleotide comprises RNA, as RNA/RNA hybrids are very stable. Since one of the aims of the exon skipping technique is to direct splicing in subjects it is preferred that the oligonucleotide RNA comprises a modification providing the RNA with an additional property, for instance resistance to endonucleases and RNaseH, additional hybridisation strength, increased stability (for instance in a bodily fluid), increased or decreased flexibility, reduced toxicity, increased intracellular transport, tissue-specificity, etc. Preferably said modification comprises a 2'-O-methyl-phosphorothioate oligoribonucleotide modification. Preferably said modification comprises a 2'-O-methyl-phosphorothioate oligodeoxyribonucleotide modification, locked nucleic acid, PNA, or a morpholino modification or a combination thereof. In one embodiment the invention provides a hybrid oligonucleotide comprising an oligonucleotide comprising a 2'-O-methyl-phosphorothioate oligo(deoxy)ribonucleotide modification and locked nucleic acid. This particular combination comprises better sequence specificity compared to an equivalent consisting of locked nucleic acid, and comprises improved efficacy when compared with an oligonucleotide consisting of 2'-O-methyl-phosphorothioate oligo(deoxy)ribonucleotide modification. With the advent of nucleic acid mimicking technology it has become possible to generate molecules that have a similar, preferably the same hybridisation characteristics in kind not necessarily in amount as nucleic acid itself. Such equivalents are of course also part of the invention. Examples of such mimics equivalents are peptide nucleic acid, locked nucleic acid and/or a morpholino phosphorodiamidate. Suitable but non-limiting examples of equivalents of oligonucleotides of the invention can be found in (Wahlestedt, C. et al. (2000), Elayadi, A. N. & Corey, D. R. (2001), Larsen, H. J., Bentin, T. & Nielsen, P. E. (1999), Braasch, D. A. & Corey, D. R. (2002), Summerton, J. & Weller, D. (1997). Hybrids between one or more of the equivalents among each other and/or together with nucleic acid are of course also part of the invention. In a preferred embodiment an equivalent comprises locked nucleic acid, as locked nucleic acid displays a higher target affinity and reduced toxicity and therefore shows a higher efficiency of exon skipping. An anti-sense oligonucleotide of the invention may comprise one or more nucleotide analogues. New nucleotide analogues are currently developed as a method for treatment against viral infections. These nucleotide analogues typically though not necessarily have similar binding characteristics as the nucleotide they replace. An anti-sense oligonucleotide of the invention may incorporate such a nucleotide analogue. An anti-sense oligonucleotide of the invention preferably does not comprise more than 20% of such a nucleotide analogues. Preferably an anti-sense oligonucleotide of the invention preferably does not comprise more than 10% of such a nucleotide analogues. An anti-sense oligonucleotide of the invention preferably does not comprise more than 3 of such a nucleotide analogues. An anti-sense oligonucleotide of the invention preferably does not comprise more than 1 of such a nucleotide analogues. An oligonucleotide or functional equivalent thereof may further comprise an additional entity to provide a further function to the resulting molecule. A fluorescent tag or immune regulating compound such as a CpG island may be added to said oligonucleotide or functional equivalent thereof.

The anti-sense sequence can be delivered in vivo or ex vivo, i.e. into precursor cells (I would not mention this since the antisense can also be delivered in vivo to the endogenous precursor cells; instead). In a proffered embodiment, the precursor cells containing the antisense sequences are used for cell transplantation therapies. In a preferred embodiment said compound comprises an anti-sense molecule or a functional equivalent thereof. A functional equivalent of an anti-sense molecule of the invention has the same expression inhibiting effect in kind not necessarily in amount, as said anti-sense molecule. The anti-sense molecule or the functional equivalent thereof can be designed in various ways. Reference is made to [1] and references therein for details about the design of anti-sense molecules. This reference and the references therein are therefore herein incorporated by reference. Lowering or down-regulating expression of an aberrantly expressed gene typically results in decreased levels of gene product encoded by said gene in said cell. Said gene product is preferably RNA produced by said gene, for instance a microRNA.

In another preferred embodiment said compound comprises a protein capable of inhibiting and/or antagonizing the function of said aberrantly expressed gene. In a preferred embodiment said compound comprises noggin or a functional part, derivative and/or analogue thereof. Noggin is capable of inhibiting and/or antagonizing the function of BMP-4[5]. A BMP-4 antagonist inhibits the function of BMP-4. Other BMP-4 inhibitors/antagonists of the invention are: chordin, ventroptin, twisted gastrulation, gremlin or other members of the DAN family of BMP4 antagonists, PRDC, sclerostin, CTGF and follistatin. Thus in a preferred embodiment the invention provides use of a BMP-4 antagonist (for antagonizing expression of BMP4 in a cell), for the manufacture of a medicament for alleviating a symptom of a genetic muscular dystrophy in an individual. Preferably said antagonist comprises noggin, chordin, ventroptin, twisted gastrulation, gremlin or other members of the DAN family of BMP4 antagonists, PRDC, sclerostin, CTGF and/or follistatin or a functional part, derivative and/or analogue of said protein. Said antagonist may be provided as protein or as a nucleic acid comprising an expression cassette for expression of said antagonist in a cell. In this latter embodiment a compound of the invention preferably comprises said expression cassette for expression of said antagonist in a cell. Further provided is a method for stimulating differentiation of a myoblast cell comprising providing and/or contacting said myoblast cell with a BMP-4 antagonist. Further provided is a method for stimulating differentiation of a myoblast cell comprising providing said myoblast cell with a nucleic acid comprising an expression cassette for expression of said antagonist in said cell. Providing a neighbouring cell with such an expression cassette is considered to be providing and/or contacting the adjacent myoblast cell with said BMP-4 antagonist, i.e. the protein. In a preferred embodiment said neighbouring cell is a muscle cell.

There are many ways to increase expression of (an aberrantly expressed) gene in a cell. Non-limiting examples are the introduction of an expression construct comprising a coding sequence for said gene, expressing a transcription factor that activates or stimulates expression of the endogenously present gene and the expression of analogues, derivatives and/or parts of said gene in said cell. It is also possible to directly transfect protein or RNA encoded by said gene in said cell. These methods are herein collectively referred to as gene therapy. In one embodiment the invention therefore provides a use or a method, wherein modifying said expression comprises gene-therapy. Said gene therapy can be executed in an ex-vivo method or in an in-vivo method. Increasing expression of a gene product in a cell preferably results in increased levels of gene product in said cell. The starting level may be undetectable.

A muscle disorder is a disease that usually has a significant impact on the life of an individual. Any measure that can be taken to alleviate consequences of a muscle disorder could therefore mean a relief for an individual with said muscle disorder. As differentiated muscle cells are replenished and/or regenerated through myoblast precursor cells, the present invention is particularly suited for the treatment of muscle disorders. The invention provides a use or a method according to the invention, wherein at least a part of the symptoms exhibited by said individual suffering from said genetic disease is due to abnormal differentiation of the muscle precursor cells in addition to the malfunctioning of differentiated muscle cells in said individual when compared to a healthy individual. A muscle disorder can either have a genetic cause or a non-genetic cause. A preferred example of a disease with a genetic cause is a genetic muscular dystrophy.

Genetic muscular dystrophies constitute a group of genetic disorders characterized by progressive muscle wasting and weakness. Many of these disorders are caused by defects in genes for muscle proteins. The different forms of genetic muscular dystrophies often differ in the involved protein(s). Most of the affected genes in these disorders code for proteins that seem to play a role in supporting the structure of muscle fibers, alternatively some proteins may be concerned with biochemical processes that occur in muscle fibers. The invention provides a use or a method according to the invention, wherein said genetic disease comprises a genetic muscular dystrophy. Muscular dystrophies are generally inherited although there are cases in which no family history of the disease exists. The clinical appearance of the different forms of genetic muscular dystrophies varies amongst other things in muscles first and most often affected, the rate at which symptoms progress and age of onset.

There are multiple diagnostic methods available for the diagnosis of the genetic muscular dystrophies and the differentiation between them. Most often a combination of a few methods is used to make a diagnosis. A diagnosis usually starts with an evaluation of the medical history of a patient and a physical examination. Examples of available diagnostic tests are a blood enzyme test (for example for creatine kinase, CK), assessment of muscle histology, DNA test, magnetic resonance (MR), electromyogram (EMG) and nerve conduction velocity study (NCV). The invention discloses a use or a method according to the invention, wherein said genetic muscular dystrophy is one of the following diseases: Becker Muscular Dystrophy (BMD), Congenital Muscular Dystrophy (CMD), Distal Muscular Dystrophy (DD), Duchenne Muscular Dystrophy (DMD), Emery-Dreifuss Muscular Dystrophy (EDMD), Facioscapulohumeral Muscular Dystrophy (FSH), Limb-Girdle Muscular Dystrophy (LGMD), Myotonic Dystrophy (MMD), Oculopharyngeal Muscular Dystrophy (OPMD). A short description of the causes of aforementioned genetic muscular dystrophies is given below.

Becker Muscular Dystrophy (BMD), insufficient production of functional dystrophin, a protein that helps keep muscle cells intact.

Congenital Muscular Dystrophy (CMD), genetic mutations affecting some of the proteins necessary for muscles and sometimes for the eyes and/or brain.

Distal Muscular Dystrophy (DD), a mutation in any of at least seven genes that affect proteins necessary to the function of muscles.

Duchenne Muscular Dystrophy (DMD), absence of dystrophin, a protein that helps keep muscle cells intact.

Emery-Dreifuss Muscular Dystrophy (EDMD), mutations in the genes that produce emerin, lamin A or lamin C, proteins in the membrane that surrounds the nucleus of each muscle cell.

Facioscapulohumeral Muscular Dystrophy (FSH), a missing piece of DNA on chromosome 4.

Limb-Girdle Muscular. Dystrophy (LGMD), a mutation in any of at least 15 different genes that affect proteins necessary for muscle function.

Myotonic Dystrophy (MMD), a repeated section of DNA on either chromosome 19 or chromosome 3.

Oculopharyngeal Muscular Dystrophy (OPMD), a faulty gene for poly(A)-binding protein 1 (PABPN1), which is suspected to aggregation of RNA and proteins in the nuclei of muscle cells.

In both Duchenne and Becker muscular dystrophy the muscle protein dystrophin is affected. In Duchenne dystrophin is absent, whereas in Becker some dystrophin is present but its production is most often not sufficient and/or the dystrophin present is abnormally formed. Both diseases are associated with recessive X-linked inheritance. DMD results from a frameshift mutation in the DMD gene [6;7]. The frameshift in the DMD gene results in the production of a truncated non-functional Dystrophin protein[8]. BMD occurs as a consequence of multiple mutations in the DMD gene. As in Becker some dystrophin is present in contrast to Duchenne where dystrophin is absent, Becker has less severe symptoms then Duchenne. The onset of DMD is earlier than BMD. DMD usually manifests itself in early childhood, BMD in the teens or in early adulthood. The progression of Becker is slower and less predictable than Duchenne. Patients with BMD can survive into mid to late adulthood. Patients with Duchenne rarely survive beyond their thirties.

Dystrophin plays an important structural role in the muscle fiber, connecting the extracellular matrix and the cytoskeleton. The N-terminal region binds actin, whereas the C-terminal end is part of the dystrophin glycoprotein complex (DGC), which spans the sarcolemma[9]. In the absence of dystrophin, mechanical stress leads to sarcolemmal ruptures, causing an uncontrolled influx of calcium into the muscle fiber interior, thereby triggering calcium-activated proteases and fiber necrosis[10].

A precursor of a differentiated cell has specific characteristics which makes it differentiate into a cell with specific functions. These specific characteristics comprise the presence and activation state of a category of genes that is involved in the control of the differentiation of a cell. In the present invention it has been found that particularly controlling genes add to the symptoms of the genetic defect when aberrantly expressed in the precursor cell. In a preferred embodiment said aberrantly expressed gene comprises Bone Morphogenetic protein 4 (BMP4). Bone Morphogenetic Proteins (BMPs) are regulatory factors that are members of the transforming growth factor-beta superfamily of proteins. They are synthesized as large precursor molecules which are cleaved by proteolytic enzymes. The active form can consist of a dimer of two identical proteins or a heterodimer of two related bone morphogenetic proteins. Bone Morphogenetic Proteins are implicated in a large variety of cellular processes [12]. BMPs are involved in the differentiation of certain cell types, including myogenic cells. In one preferred embodiment the invention provides a use or a method according to the invention, wherein said transforming growth factor-beta is a Bone Morphogenetic Protein (BMP) or a functional part, derivative and/or analogue thereof, preferably BMP4 or a functional part, derivative and/or analogue thereof.

In another aspect the invention provides a use or a method according to the invention, wherein said aberrantly expressed gene is a controlling factor in the differentiation of said precursor cell into said differentiated cell. A controlling factor is a factor which controls alone, or with other controlling factors, at least one step in the differentiation of a precursor cell into a differentiated cell. Control of said at least one step in the differentiation can be stimulatory or inhibitory. Said controlling factor realizes this control through being part of a signal-transduction cascade. Said controlling factor preferably is located at the beginning of said signal-transduction cascade, receiving signals that come from, for instance, outside the cell in which said cascade is located. In another preferred embodiment of the invention said controlling factor is located at the end of said signal-transduction cascade, effecting signals that are transduced by said cascade. A controlling factor is for example a growth factor or a transcription factor.

A growth factor is a small protein that attaches to specific receptors on the surface of cells and promote proliferation, growth, differentiation and/or maturation of these cells. Examples of growth factors are: granulocyte-colony stimulating factor (G-CSF); granulocyte-macrophage colony stimulating factor (GM-CSF); platelet-derived growth factor (PDGF); erythropoietin (EPO); thrombopoietin (TPO); myostatin (GDF-8) and/or fibroblast growth factor 2 (FGF-2). In a preferred embodiment the invention provides a use or a method according to the invention, wherein said controlling factor comprises a growth factor or a functional part, derivative and/or analogue thereof, preferably fibroblast growth factor (FGF2) or insulin-like growth factor binding protein (IGFBP3), BMP4, or a functional part, derivative and/or analogue thereof. Fibroblast Growth Factor 2 (FGF2) is a single-chain polypeptide growth factor that plays a significant role in the process of wound healing and is a potent inducer of angiogenesis. Several different forms of the human protein exist ranging from 18-24 kDa in size due to the use of alternative start sites within the fgf-2 gene. It has a 55 percent amino acid residue identity to fibroblast growth factor 1 and has potent heparin-binding activity. The growth factor is an extremely potent inducer of DNA synthesis in a variety of cell types from mesoderm and neuroectoderm lineages.

Insulin-Like Growth Factor II is a multiplication-stimulating factor. It is a well-characterized neutral peptide believed to be secreted by the liver and to circulate in the blood. It has growth-regulating, insulin-like and mitogenic activities. Insulin-Like Growth Factor Binding Protein 3 (IGFBP3) is one of the six homologous soluble proteins that bind insulin-like growth factors (somatomedins) and modulate their mitogenic and metabolic actions at the cellular level.

Transforming growth factor (TGF) is one of many characterized growth factors that exist in nature. Transforming Growth Factors are hormonally active polypeptides that can induce the transformed phenotype when added to normal, non-transformed cells. Their transforming activities are due to the simultaneous action of two otherwise unrelated factors, transforming growth factor alpha and transforming growth factor beta. In a preferred embodiment the invention provides a use or a method according to the invention, wherein said growth factor belongs to the transforming growth factor-β (TGFβ) superfamily or is a functional part, derivative and/or analogue thereof. TGFβ is a factor synthesized in a wide variety of tissues. It acts synergistically with TGF-alpha in inducing phenotypic transformation and can also act as a negative autocrine growth factor. TGF-beta has a role in embryonal development, cellular differentiation, hormone secretion, and immune function. TGF-beta is found mostly as homodimer forms of separate gene products TGF-beta1, TGF-beta2 or TGF-beta3. Heterodimers composed of TGF-beta1 and 2 (TGF-beta1.2) or of TGF-beta2 and 3 (TGF-beta2.3) have been isolated. The TGF-beta proteins are synthesized as precursor proteins. Transforming growth factor alpha is a factor that has been isolated in a variety of tissues including epithelium, and maternal decidua. It is closely related to epidermal growth factor and binds to the EGF receptor. TGF-alpha acts synergistically with TGF-beta in inducing phenotypic transformation, but its physiological role is unknown.

Myostatin (also known as Growth and Differentiation Factor 8) is a growth factor that limits muscle tissue growth, i.e.

higher concentrations of myostatin in the body cause the individual to have lesser developed muscles. The myostatin protein is produced in muscle cells, circulates in the blood and acts on muscle tissue, apparently by slowing down the development of muscle stem cells[11]. Myostatin is a member of the TGF-beta superfamily of proteins. In a preferred embodiment the invention provides a use and a method according to the invention, wherein said controlling factor comprises myostatin.

Mechanisms that regulate cell differentiation also involve transcription factors. In one embodiment the invention provides a use or a method according to the invention, wherein said controlling factor comprises a transcription factor. A transcription factor is a protein needed to initiate the transcription of a gene. Transcription factors can be tissue-specific, which means that those factors only have a function in the transcription of one or a few specific gene(s). Alternatively the transcription factors can be general, being involved in the start of transcription of many different genes.

In a particularly preferred embodiment, a method or use of the invention is combined with another treatment for the genetic defect. As a first example, in genetic defects that are the result of an absent or dysfunctional gene product in a differentiated cell, a method or use of the invention is preferably combined with a method for enhancing expression of the absent or dysfunctional gene product in the differentiated cell. Thus the invention further provides a use or a method according to the invention, further comprising providing said individual with a medicament for providing said differentiated cell with at least part of the normal function of said mutated gene. As a second example, in genetic defects that are the result of an absent or dysfunctional gene product in a differentiated cell, a method or use of the invention is preferably combined with a method that uses transplantation of precursor cells for said differentiated cells to the patient in order to generate new and functional differentiated cells. The precursor cells may be derived from healthy donors, but in that case the risk of rejection is high[13]. Therefore, precursor cells derived from the patient are preferred. Said precursor cells are genetically changed ex vivo to express a functional copy of the gene affected by the mutation. The invention provides a method to correct other defects in the precursor cells secondary to the genetic mutation, and enhances the differentiation capacity of said precursor cells in vivo.

In a further embodiment the invention provides a use or method according to the invention, wherein said aberrantly expressed gene is identified by comparing an expression profile of said precursor cell of an individual suffering from a genetic defect with a corresponding precursor cell of a healthy individual. A gene is said to be aberrantly expressed when it is at least 2-fold differentially expressed compared to said corresponding precursor cell in said healthy individual.

In an example of the invention, a large-scale gene expression time course study using primary human myoblast cultures is performed, wherein myogenesis in DMD cells and the first reaction of the differentiating cell to the absence of dystrophin are monitored. The results show a clear phasing of the different stages in myogenesis. Already at the myoblast stage differences appear and although differentiation seems to initiate at the same time in healthy and DMD cultures, it is shown that the DMD cells differentiate less efficiently. Studies have been performed previously which used gene expression profiling to find pathways involved in the disease mechanism[14-16]. These studies however, did not analyze molecular differences at the precursor cell (myoblast) level but were all focussed on the differentiated cell (muscle cell) itself.

As a preferred example of the invention significant differences in gene expression between healthy and DMD cell cultures have been observed. This observation would not have been expected as the full-length dystrophin is not yet expressed in myoblasts and Dp71 myoblast expression should not be hampered by the mutations as they are located upstream of the translation initiation site[17]. One of the differentially expressed genes, Fibroblast growth factor 2 (FGF2) is significantly lower expressed in DMD myoblasts. In vitro and in vivo studies demonstrated an important role for FGF2 in the recruitment of satellite cells into proliferation. The addition of recombinant FGF2 enhanced the number of proliferating myoblasts by twofold and did not suppress the initiation of differentiation[18-20]. In addition, Doukas et al. demonstrated that targeted transgene delivery of FGF2 and FGF6 genes led to an enhancement of skeletal muscle repair, showing the importance of the FGF genes in regeneration [21]. These observations indicate that the lower DMD myoblast FGF2 expression observed in an example of the invention, can explain the decreased myoblast proliferation in DMD cultures previously reported[22-24].

Although proliferation capacity is probably reduced and differentiation inhibited in DMD cell cultures, the results of an example of the invention indicate that the timing of the different processes is similar. Genes involved in proliferation are simultaneously downregulated after fusion induction in both healthy and DMD cell cultures (MCM6, CCNB2, CDC28, CKS2 and RPA3, FIG. 5, group 'cell growth and maintenance'). During the actual fusion process of myoblasts into myotubes however, gene expression differences appear between healthy and DMD cell cultures, again pointing at an impaired fusion potential of DMD cells. In an example of the invention genes have been found to be aberrantly expressed that are involved in fusion of healthy myoblasts but that probably do not participate in DMD myoblast fusion. Of these, Membrane metallo-endopeptidase (MME) and Adlican (DKFZp564I1922) are thought to be involved in cell adhesion and cell-cell signalling, which are important for cell fusion[25]. In the gene expression study, Laminin alpha 2 (LAMA2) is continuously lower expressed in DMD cell cultures, making them less adhesion competent. This explains the absence of the Laminin alpha 2 dependent adhesion force which has been reported previously by Angoli et al. [26].

Surprisingly, Mitochondrial tumor suppressor 1 (MTUS1) and Endothelin receptor type A (EDNRA), both presumed to be involved in signalling, are only upregulated in the DMD cells upon initiation of differentiation. These genes are possibly part of alternative signalling pathways due to the absence of Dystrophin.

In a time-course study, differentiation and fusion of primary human myoblasts into myotubes takes approximately 4 days. After this, almost no expression changes are visible and genes are stably expressed[27]. A striking phenomenon is the upregulation of the sarcomeric gene expression after initiation of differentiation in both healthy and DMD cell cultures and a subsequent significant decline, starting at day 6, detectable in DMD myotubes only. The absence of dystrophin causes sarcomeric instability, resulting in a secondary response which initiates downregulation of structural genes. Other functional classes of proteins that are simultaneously up or down-regulated during myoblast differentiation do not show a difference in the later timepoints, indicating that this negative feedback is a unique characteristic of the sarcomeric proteins in DMD cultures.

Two present promising gene therapies are based on the re-establishment of dystrophin in the DGC complex by either AAV-mediated introduction of a micro-DMD gene or by skipping an exon to restore the reading frame of the gene[28-36]. The results of an example of the invention indicate that the effectiveness of these therapies might not fulfill the present expectations. Thus far, studies focussed on the dystrophin protein and its localization, but did not look specifically at the regeneration capacity of the muscle after therapy. The presence of dystrophin only corrects the sarcomeric instability and might just alleviate (temporarily) but not cure the patients because regeneration signalling pathways are not restored. From this viewpoint, it would be crucial to start therapy early in life, before these changes have taken place. Alternatively, additional (pharmaceutical) intervention to regain the normal muscle regeneration capacity should be pursued. A use or a method according to the invention could be applied in combination with a promising gene therapy. In one embodiment the invention provides a use or a method according to the invention, wherein said genetic muscular dystrophy is Becker Muscular Dystrophy (BMD) or Duchenne Muscular Dystrophy (DMD). In a preferred embodiment the invention provides a use or a method according to the invention, comprising skipping an exon of a dystrophin gene. An example of the invention shows molecular differences between healthy and DMD myoblasts during myogenesis. Decreased FGF2 levels and elevated expression of BMP4 in DMD myoblasts reduce proliferation capacity and make them less differentiation competent. In addition, lower expression of sarcomeric proteins in DMD myotubes is observed. This combination of reduced proliferation, impaired fusion and impaired maintenance of the DMD myotubes leads to inefficient muscle regeneration and contributes to the severe phenotype of DMD patients.

Transplantation of ex vivo expanded myoblasts to DMD patients is an alternative and promising therapy[37]. There are at least two options. Treatment with myoblasts from healthy subjects or autologous cell transplantation. In the first case, the rejection of the cells by the host due to the induction of an immune response is a major concern[13]. Immunocompatible donors, preferably family members[37;38], or immunosuppressants[39;40] are employed to control this immune response. Autologous cell transplantation has the advantage of a reduced chance of rejection by the immune system. Before autologous transplantation, the gene defect has to be corrected by introduction of a functional transgene[41] or an expression cassette that produces exon skipping antisense sequences[4]. In an example of the invention, a microDMD gene is introduced using an recombinant AAV. In one embodiment the invention provides a use or a method according to the invention of an antisense oligonucleotide or siRNA against BMP4 to reduce the expression of BMP4 in autologous myoblasts, and to enhance the regenerative potential of said autologous myoblasts in a patient.

The invention further provides the use of a compound for modifying expression of a gene, for the manufacture of a medicament for alleviating a symptom of a genetic disease in an individual, wherein said disease is the result of a genetic defect in a differentiated cell of said individual, wherein said gene is aberrantly expressed in a precursor of said differentiated cell and wherein said aberrant expression is not directly related to the mutation underlying said genetic defect. In a preferred embodiment said mutation underlying said genetic defect is associated with a gene and is a result of no or defective protein synthesis from said gene (mutated gene). In a further preferred embodiment modifying said expression comprises lowering expression when said aberrantly expressed gene is over-expressed in said precursor cell and elevating expression when said aberrantly expressed gene is under-expressed in said precursor cell. In a preferred embodiment said aberrantly expressed gene is a controlling factor in the differentiation of said precursor cell into said differentiated cell. Preferably said controlling factor comprises a growth factor or a functional part, derivative and/or analogue thereof. Preferably said growth factor belongs to the transforming growth factor-β (TGFβ) superfamily or is a functional part, derivative and/or analogue thereof. Preferably said growth factor belonging to the transforming growth factor-beta superfamily is Bone Morphogenetic Protein 4 (BMP4) or a functional part, derivative and/or analogue thereof. Preferably said controlling factor comprises a (transcription) factor that influences the expression of said aberrantly expressed gene.

The invention further provides a method for stimulating differentiation of myoblast cells comprising providing said myoblast cells with a compound for inhibiting expression of a growth factor in said myoblast cells. Preferably said inhibition comprises inhibiting BMP-4 mRNA expression in said myoblast cells. Preferably said method further comprises contacting said myoblast cells with mature muscle cells. Preferably said mature muscle cells are derived from a subject that suffers from a genetic muscular dystrophy. Preferably said contacting is done by transplanting said myoblast cells into said individual. Preferably said transplanted myoblast cells are from a matched donor. Preferably, the myoblast cells are autologous myoblast cells. Preferably inhibiting BMP-4 mRNA expression in said myoblast cells comprises providing said myoblast cells or precursors thereof with a BMP-4 oligonucleotide that is complementary to said BMP-4 gene (anti-sense). Preferably said myoblast cells or precursors thereof are in vitro provided with said BMP-4 anti-sense oligonucleotide. The invention further provides a collection myoblast cells or precursors thereof comprising a BMP-4 anti-sense oligonucleotide.

Further provided is a use or a method of the invention wherein said precursor is a myoblast or a precursor thereof. Preferably said expression is inhibited by means of a virally transduced DNA sequence. Preferably said genetic disease comprises a genetic muscular dystrophy. Preferably said genetic muscular dystrophy comprises one of the following diseases: Duchenne Muscular Dystrophy (DMD), Becker Muscular Dystrophy (BMD), Congenital Muscular Dystrophy (CMD), Distal Muscular Dystrophy (DD), Emery-Dreifuss Muscular Dystrophy (EDMD), Facioscapulohumeral Muscular Dystrophy (FSH), Limb-Girdle Muscular Dystrophy (LGMD), Myotonic Dystrophy (MMD), Oculopharyngeal Muscular Dystrophy (OPMD). Preferably said compound comprises a protein inhibitor. Preferably wherein said protein inhibitor comprises a growth factor inhibitor or antagonist, preferably a BMP-4 inhibitor or antagonist, preferably wherein said inhibitor or antagonist comprises noggin, chordin, ventroptin, twisted gastrulation, gremlin or other members of the DAN family of BMP4 antagonists, PRDC, sclerostin, CTGF and/or follistatin or a functional part, derivative and/or analogue or a functional part, derivative and/or analogue thereof.

Preferably a method or use of the invention further comprises use of a second compound for the preparation of a medicament of for treatment of said individual wherein said second compound provides said differentiated cell with at least part of the normal function of said mutated gene. Preferably said genetic muscular dystrophy is Duchenne Muscular Dystrophy (DMD) or Becker Muscular Dystrophy (BMD). Preferably said second compound comprises an oligonucleotide, or functional equivalent thereof, for skipping an exon of a dystrophin gene. Preferably said second compound comprises an oligonucleotide or functional equivalent thereof complementary to an exon of a dystrophin gene.

In a preferred aspect the invention provides the use of a compound for reducing, inhibiting and/or antagonizing expression of Bone Morphogenetic Protein 4 (BMP4) in a cell, for the manufacture of a medicament for alleviating a symptom of a genetic muscular dystrophy in an individual. Preferably said cell is a myoblast cell or a precursor thereof. Preferably said compound comprises an antisense RNA or a functional equivalent thereof.

The invention further provides a method for stimulating differentiation of a myoblast cell comprising providing said myoblast cell with a compound for reducing, inhibiting and/or antagonizing expression of BMP4 in said myoblast cell. Preferably said compound (is capable of reducing and/or inhibiting) decreases and/or inhibits BMP4 mRNA expression in said myoblast cell. In another preferred embodiment said compound (is capable of antagonizing) antagonizes the function of BMP-4. A use and/or method according to the invention further comprises contacting said myoblast cell with a mature muscle cell. In a preferred embodiment said mature muscle cell is derived from a subject that suffers from said genetic muscular dystrophy. A method of the invention for reducing and/or inhibiting BMP4 mRNA expression in said myoblast cell comprises providing said myoblast cell or a precursor thereof with a BMP4 oligonucleotide that is complementary to said BMP4 gene (anti-sense). Preferably said myoblast cells or precursors thereof are in vitro provided with said BMP-4 anti-sense oligonucleotide.

The invention further provides a collection of myoblast cells or precursors thereof comprising a BMP-4 anti-sense oligonucleotide.

Reducing and/or inhibiting expression of BMP4 is preferably achieved by means of a virally transduced DNA sequence. Preferably said compound is provided to said cell by means of a viral vector. Preferably said genetic muscular dystrophy comprises one of the following diseases: Duchenne Muscular Dystrophy (DMD), Becker Muscular Dystrophy (BMD), Congenital Muscular Dystrophy (CMD), Distal Muscular Dystrophy (DD), Emery-Dreifuss Muscular Dystrophy (EDMD), Facioscapulohumeral Muscular Dystrophy (FSH), Limb-Girdle Muscular Dystrophy (LGMD), Myotonic Dystrophy (MMD), Oculopharyngeal Muscular Dystrophy (OPMD). Preferably said compound comprises a protein inhibitor. Preferably said compound comprises a BMP4 inhibitor or antagonist. Preferably said inhibitor or antagonist comprises noggin, chordin, ventroptin, twisted gastrulation, gremlin or other members of the DAN family of BMP4 antagonists, PRDC, sclerostin, CTGF and/or follistatin or a functional part, derivative and/or analogue or a functional part, derivative and/or analogue thereof. Preferably a method or use of the invention further comprises use of a second compound for the preparation of a medicament for treatment of said individual wherein said second compound provides a muscle cell of said individual with at least part of the normal function of a gene that is associated with said genetic muscular dystrophy (mutated gene). Preferably said genetic muscular dystrophy is Duchenne Muscular Dystrophy (DMD) or Becker Muscular Dystrophy (BMD). Preferably said second compound comprises an oligonucleotide, or functional equivalent thereof, for skipping an exon of a dystrophin gene.

In a further aspect the invention provides a method for determining whether a BMP4 anti-sense oligonucleotide or a functional equivalent thereof is capable of inducing skipping of an exon in a BMP4 pre-mRNA containing said exon, said method comprising providing a cell expression said BMP4 pre-mRNA with said oligonucleotide and determining whether said exon is absent from mature mRNA produced from said pre-mRNA. Preferably, the skipping of an exon in the BMP4 mRNA reduces the production level of functional BMP4 protein levels. Exon skipping in BMP4 and DMD has different objectives: reading frame disruption (or exclusion of an essential stretch of amino acids; BMP4) vs reading frame correction (DMD). A oligonucleotide or functional equivalent thereof is said to be effective in inducing skipping of said exon, if more than 5 and preferably more than 10% of the mRNA resulting from splicing of said pre-mRNA in said method does not contain said exon, as measured in vitro by means of an nucleic acid amplification reaction (preferably polymerase chain reaction, PCR) with primers in exons flanking said exon (that is targeted by said anti-sense oligonucleotide or functional equivalent thereof). Preferably said anti-sense oligonucleotide or a functional equivalent thereof is complementary to said exon. In a particularly preferred embodiment said anti-sense oligonucleotide or a functional equivalent thereof is complementary to an exon-internal part of said exon. An exon-internal part of said exon is herein defined as a part that is complementary to said exon and that does not include intronic sequence immediately flanking said exon. Preferably said exon-internal oligonucleotide or functional equivalent thereof does not comprise one or both of the two exon splice acceptor and/or exon splice donor nucleotides flanking said exon. Preferably said anti-sense oligonucleotide or a functional equivalent thereof is complementary to exon 4 of BMP4. Some BMP4 transcripts start in exon-2. Alternative splice variants may also exist. In these case the numbering of the exons is counted from the exon identified by AON hBMP4#2, and this exon is given the number 4 also if the actual number of exons included in the mRNA before exon 4 is lower or higher than 3. The invention further provides oligonucleotide having the sequence of AON hBMP4#2.

The invention further provides the use of an anti-sense oligonucleotide or a functional equivalent thereof that is complementary to an exon of BMP-4, for skipping said exon in a BMP4 pre-mRNA. An anti-sense oligonucleotide or a functional equivalent thereof is complementary to an exon of BMP-4 for use in the treatment of a genetic muscular dystrophy. Further provided is the use of an anti-sense oligonucleotide or a functional equivalent thereof is complementary to an exon of BMP-4 for the preparation of a medicament for the treatment of a genetic muscular dystrophy. Said anti-sense oligonucleotide or functional equivalent thereof can be provided to said cell by a number of different methods. A preferred method is without any means for enhancing transfer of said oligonucleotide or functional equivalent thereof to said cell. This is particularly preferred in case of in vivo administration of said oligonucleotide or functional equivalent thereof. In another preferred embodiment said anti-sense oligonucleotide is provided to said cell by means of a viral vector. In a preferred embodiment said viral vector comprises an expression cassette for expression of said anti-sense oligonucleotide.

EXAMPLES

Example 1

Material and Methods

Cell Culture

Primary human myoblasts were isolated from skeletal muscle biopsies [42] of three healthy individuals (KM109, KM108 and HPP4) and three DMD patients (DL589.2 [exon 51-55 deletion], DL470.2 [exon 46-50 deletion] and 50685.1 [exon 48-50 deletion])[42;43]. The age at time of biopsy varied from 2-14 years. The cultures consist of myoblasts and other cell types that were present in the original biopsy. The proportion of myoblasts was determined for each biopsy by desmin staining and cell counting as described[44]. Healthy and DMD cultures did not differ in the average percentage of myoblasts (57±20%). Cells were grown in proliferation medium in collagen-coated culture flasks. When cells were 80% confluent, differentiation was initiated by replacing the high-serum medium with low-serum medium[27]. All cell cultures used for the experiments had passage numbers between 4 and 10.

cDNA Hybridization cDNA microarrays containing 4417 muscle-related genes and ESTs (spotted in triplicate) from a human sequence-verified 40K I.M.AG.E. cDNA library (Research Genetics) were used and these were PCR-amplified, printed and pre-hybridized as described[27;45]. Total RNA from the six different cell cultures was isolated at days 0, 1, 2, 4, 6, 10 and 14, amplified, labeled and co-hybridized with a common reference as described[27;45]. The quality and quantity of the total RNA and cRNA was checked with the Bioanalyzer Lab-on-a-Chip RNA nano assay (Agilent Technologies).

Data Analysis

All slides were scanned with an Agilent scanner (Model 2565BA) and spot intensities were quantified with the Gene-Pix Pro 3.0 program (Axon Instruments). Raw intensity files were imported into Rosetta Resolver® v4.0 (Rosetta Biosoftware) and normalized with the Axon/Genepix error model. Per condition (healthy or DMD), 9 measurements per gene were considered (3 biological replicates, 3 technical replicates) and a stringent data-analysis procedure was performed. Genes with a normalized intensity higher than the average+2 standard deviations (SDs) of the negative array controls, were analyzed. This had to be consistent in one condition (healthy or DMD) and in at least one timepoint. Error-weighted two-way ANOVA was performed with time, disease state and the interaction between time and disease state as variables. Genes were considered differentially expressed when the P-value for disease state was $<1\times10-5$ (Bonferroni corrected). Genes differentially expressed in time ($P<1\times10-5$) were functionally divided into groups using Gene Ontology Tree Machine [46].

Quantitative RT-PCR cDNA was prepared from total RNA of all 6 cell cultures by reverse transcription using random hexamers and 0.5 mg total RNA as template. PCR primer pairs were designed using Primer3 (http://www-genome.wi.mit.edu/cgi-bin/primer/primer3.cgi/). The oligonucleotide primer pairs used for each of the genes in this study correspond to the following nucleotides: glyceralde-hyde-3-phospate dehydrogenase, 510-529 and 625-644 (NM_002046); BMP4 394-413 and 484-503 (NM_001202) and AQP1 1129-1148 and 1227-1246 (NM_198098.1). Quantitative PCRs (Lightcycler, Roche) were performed as described with an annealing temperature of 58° C. (for GAPDH and BMP4) or 62° C. (for AQP1)[27]. Optimal cDNA dilutions and relative concentrations were determined using a dilution series per gene. Each gene was normalized to the abundance of glyceraldehyde-3-phosphate dehydrogenase mRNA (shows constant expression over time on the arrays).

RT-MLPA

MLPA probes were designed following the criteria described in[47]. The reaction was carried out on 50 ng total RNA as described in[48], except that all oligonucleotides used as half probes were chemically synthesized (Illumina Inc, San Diego), and two fluorophores were used during the PCR reaction[49]. Two ml of labelled PCR product was mixed with 10 ml formamide and 0.05 ml ROX500 size standard and separated on an ABI3700 capillary sequencer (Applied Biosystems). As there was a considerable range in peak heights 1:10 dilutions were loaded where necessary to obtain sufficient non-saturated signals. Data was exported to Excel for further analysis.

For each probe the relative peak height was used as a measure of intensity. Normalization was performed by dividing the relative peak height of each probe by the sum of the peak height of two control probes amplified with the same fluorophore. The control probes were targeted to genes that showed no significant change in expression level in the array analysis (Calnexin and Protein phosphatase 3 regulatory subunit B). Standard error was calculated on basis of 6 measurements (3 cultures measured in duplicate).

Differentiation Assay and Immunohistochemical Analysis

Recombinant Human BMP4 (R&D Systems Inc.) was added to the cells at different concentrations (between 0.3 and 30 ng/ml) upon initiation of differentiation. During medium change, new BMP4 was added (every 4 days). Cells were fixed with 100% methanol (−20° C.) at 7 or 11 days after serum deprivation. Immunohistochemical staining was performed as described previously[44;49]. Differentiation index was calculated by dividing the number of myosin positive cells by the number of desmin positive cells (=myogenic cells able to differentiate)×100%. For the analysis, a generalized linear regression model was fitted to explain the differences in the differentiation as a function of day (7 or 11), concentration (0, 0.3, 1, 3, 10 and 30 ng/ml) and cell line (healthy and DMD). The computations were run using R 2.0.1[50]. The model included a term representing the interaction between cell line and concentration, which is the term used to identify individual concentration levels for which the cell line displayed statistically significant differentiation proportions. Probability distributions were associated with the (model) error, and both normal and binominal error distribution were calculated.

Results

To explore the differentiating potential of human DMD myoblasts, a large-scale gene expression analysis has been performed. Human primary skeletal muscle cell cultures of 6 different individuals (3 healthy, 3 DMD) were analyzed with a muscle-related cDNA array. RNA was isolated at the myoblast stage (day 0) and at different days of differentiation (day 1, 2, 4, 6, 10 and 14). To find genes differentially expressed, an error-weighted two-way ANOVA was performed with time, disease state and the interaction between time and disease state as variables. Of the 4010 unique genes present on the array, 2423 gave a significant signal on at least one timepoint in either all the healthy samples or all the DMD samples. 94 genes were differentially expressed between healthy and DMD cultures (52 down, 42 up in DMD, p (disease state) $<1\cdot10$-5). Surprisingly, already in undifferentiated cells (t=0), 7 genes showed more than a 2-fold difference in RNA expression level (Table 1 and Supplemental Table 1a/b). Two of these (AQP1 and BMP4), are continuously higher expressed in DMD over the whole time course. This difference was confirmed with quantitative RT-PCR (FIG. 1).

Dahlqvist et al, previously demonstrated in immortalized mouse myoblasts (C2C12) that BMP4 has an inhibitory effect on muscle differentiation[51]. To determine if this holds true in primary human myoblast cultures and to find out if healthy and DMD cells respond differently, recombinant BMP4 was added to the cells. Addition of recombinant BMP4 to the fusion medium at t=−0 resulted in a concentration-dependent reduction of cell fusion (less multinucleated, myosin-positive cells) in both healthy and DMD cell cultures (FIG. 2, 3 and FIG. 7). DMD cells were significantly more sensitive to BMP4 (p<0.05) since a 3-fold lower concentration causes a similar degree of differentiation inhibition (Table 2 and 3). The results presented correspond to using the normal distribution as error distribution (both normal and binominal error distributions yielded similar conclusions).

Along with genes that were differentially expressed between healthy and DMD over the whole time course, there was a small group of genes whose expression patterns start to diverge after induction of differentiation (p (disease state) <1.10-5). FIG. 4 shows that these genes can be divided into two groups. Firstly, genes upregulated during the fusion in healthy cell cultures that remain low in DMD cultures (BF, Adlican and MME). Secondly, two genes with a constant low expression level in healthy cell cultures, but upregulated during fusion of DMD cells (MTUS1 and EDNRA). These results were confirmed with RT-MLPA (FIG. 8). The RT-MLPA is a technique that allows the rapid and simultaneous quantification of up to 40 transcripts in a single reaction. This technique was chosen as it allows multiple samples and transcripts to be tested in a faster and cheaper assay than quantitative RT-PCR.

The two-way ANOVA also reveals genes whose expression changes equally in the timecourse of both healthy and DMD cultures (n=68, p (time)<1·10-5). The role of these genes in myogenesis has been discussed in a previous paper[27]. Using Gene Ontology Tree Machine, these genes were functionally annotated[46]. FIG. 5 shows the average expression patterns for healthy and DMD cells (functional groups containing ≧6 genes). The sarcomeric proteins (n=10) showed a significantly decreased expression at later time points in DMD compared to healthy cells (paired T-test, p<0.01). Other functional categories showed similar expression pattern changes in healthy and DMD cultures.

Example 2

Downregulation of BMP4 Expression in Duchenne Myoblasts by Exon Skipping AONs

Human myoblasts, isolated from a skeletal muscle biopsy of a Duchenne patient (DL589.2) were proliferated in 6-well dishes to a confluency of 50% (for details see example 1). Twenty four hours before transfection, cells were put on low-serum differentiation medium. Cells were transfected with the AONs (2'-O-methyl phosphorothioate) mentioned below, at a concentration of 100, 200, or 500 nM, or left untreated:
AON Sequences

```
hBMP4-#1:
5' gca ugg cuc gcg ccu ccu agc ag 3'
(SEQ ID NO: 1)

hBMP4-#2:
5' cca gug cug ugg auc ugc ucu u 3'
(SEQ ID NO: 2)

FAM-AON:
5'-FAM-cuu cca cau ccg guu guu u 3'
(SEQ ID NO: 3)
```

The first two oligonucleotides are designed against exon internal sequences in exon 4 of human BMP4, transcript variant 1 (NM_001202). The last oligonucleotide is a control oligonucleotide which should not affect BMP4 expression, and contains a 5' FAM-label to allow fluorescent detection of oligonucleotide uptake.

AONs were transfected with the Exgen500 transfection reagent (MBI Fermentas, 2 µl per µg AON). At 3 hours of transfection, the transfection complex was washed away and fresh differentiation medium was added to the cells. At 6 hours after transfection, nuclei of the FAM-AON transfected myoblasts were brightly fluorescent, indicative of high nuclear uptake of the AONs.

At 24 hours after transfection, cells were lysed in RNABee solution (Isotex Diagnostics) and RNA was isolated using the manufacturer-supplied protocol. RNA was transcribed into cDNA by incubating 200 ng of total RNA with 40 ng of random hexamer primers in 13 µl of DEPC-water for 10 minutes at 70° C. After cooling on ice, 4 µl of 5× first strand buffer, 2 µl of 10 mM dNTPs, and 1 µl of Revertaid RnaseH– reverse transcriptase (MBI Fermentas) was added and the reaction mixture was incubated at 42° C. for 2 hours. The reverse transcriptase was inactivated by incubation at 70° C. for 15 minutes. The resulting cDNA was diluted 5 times.

To evaluate AON-mediated exon skipping in the BMP4, the following PCRs were performed:
PCR1: amplification of exon 3 of the BMP4 gene, to access overall BMP4 mRNA levels. Primer sequences used: BMP4exon3for: 5'TGAGCCTTTCCAGCAAGTTTGTT 3'; (SEQ ID No: 4) BMP4exon3rev: 5' ATCAGCATTCGGT-TACCAGG 3' (SEQ ID No: 5)
PCR2: evaluation of the skipping of exon 4 by amplification with primers in exon 3 and exon 5: BMP4exon3for: 5' TGAGCTTTCCAGCAAGTTTGTT 3'; (SEQ ID No: BMP4exon5rev: 5' GGGATGCTGCTGAGGTTAAA 3' (SEQ ID No: 6)
PCR3: evaluation of cDNA synthesis with primers in GAPDH gene: GAPDH for: 5' GATCATCAGCAATGC-CTCCT 3' (SEQ ID No 7); GAPDHrev: 5' CCATCCA-CAGTCTTCTGGGT 3' (SEQ ID No: 8)

PCRs were performed with 40 cycles of 30 seconds denaturation at 94° C., 30 seconds annealing at 56° C. and 30 seconds extension at 72° C. PCR fragments were visualized on an ethidum-bromide stained agarose gel.
Results Results are displayed in FIG. 1. All three PCRs generated fragments of the expected size. AON hBMP4#2 induced skipping of exon 4 at the highest concentration tested (500 nM) (FIG. 1; Panel B), visible as a shorter fragment of 142 bp, in which exon 3 is directly spliced to exon 5. Transfection with a lower concentration of AON hBMP4#2 (200 nM) resulted in a complete absence of the BMP4 transcript. This was confirmed with the exon-internal PCR of exon 3 of the BMP4 gene (Panel A). In contrast, the control gene GAPDH is still stably expressed (Panel C), indicative of a selective loss of the BMP4 transcript. Since skipping of exon 4 disrupts the open reading frame in the BMP4 transcript, we think that exon skipping with this concentration of AON has been so effective that the transcripts is lost due to highly efficient nonsense mediated decay activity. At both concentrations, AON hBMP4#2 reduced the level of the intact BMP4 transcript and thus corrects BMP4 mRNA levels towards the normal levels in myoblast cultures from healthy subjects. AON hBMP4#1 and the control FAM-AON did not induce exon skipping. Occasionally, activation of a cryptic splice site in exon 4 was observed.

Example 3

Antisense Against BMP4 and DMD Exon Skipping Antisense Sequences in Mdx x Utrophin –/– Mice; Evaluation of Muscle Strength, Survival, Protein and RNA Levels Dystrophin and utrophin-deficient mice (mdx.utrn$^{-/-}$ mice) were generated by crossing of male mdx +/o.utrn$^{-/-}$ .hDMD+/−mice female mdx+/+.utrn−/−.hDMD+/− ('t Hoen et al, manuscript in preparation). Mice were housed under standard laboratory conditions. Animals were fed regular chow and had access to drinking water ad libitu,. 20-mer 2'-O-methyl phosphorothioate ribonucleic acids were synthesized by Eurogentec. The antisense sequences were targeted against 1. the exon 23-intron 23 boundary of the murine Dmd gene, sequence AON-1: GGCCAAACCUCGGCUUACCU (SEQ ID No: 9).

The sequence of this AON is identical to the AON used by Mann et al, and Lu et al, in their experiments in mdx mice and results in efficient skipping of the mutated exon 23 of the Dmd gene, resulting in production of functional dystrophin protein [31; 52].

2. BMP4. Designed sequences AON-2 (AGACUGGAGC-CGGUAA) (SEQ ID No: 10) and AON-3 (UGGCUCG-GCUGGCGGG) (SEQ ID No: 11) in exon 2 of mRNA sequence NM_007554.

Before injections, AONs were diluted in in 0.9% (w/v) NaCl to a final concentration of 50 mg/ml. Mice were divided randomly in three groups. The first group was injected intravenously, starting at the age of 21 days, for 5 consecutive days with 5 mg of AON-1. The second and third groups received, in addition to AON-1, 5×5 mg of AON-2 or AON-3, respectively.

Before the first injection, and 1, 2 and 3 weeks after the first injection, a blood sample was taken for determination of creatine kinase activity (a well-established bioassay for muscle damage). At these same time points, animals were forced to run on a Rotarad device and the period of time before the mice fell off was recorded (a bioassay for muscle strength). At three weeks after injection, Evans blue was administered intraperitoneally (10 mg/kg body weight) to stain damaged muscles. Mice were sacrificed by cervical dislocation, and the gastrocnemius, quadriceps, tibialis anterior, heart and diaphragm muscle were isolated and snap frozen in liquid nitrogen before further processing.

Levels of corrected dystrophin mRNA transcript were measured as described before[53]. Dystrophin protein levels were determined by Western blotting as described[53]. Standard hematoxylin/eosin staining was performed on 10 µm cryosections of the muscles to assess muscle histology. The average fibre cross-sectional area was determined. Evans blue positive areas in 10 sections per muscle were determined as a measure for muscle damage. Immunostaining with the NCL-DYS2 and CD4 antibody was performed on the sections to analyze for the presence dystrophin and the presence of immune infiltrates[53].

Example 4

Genetic Correction of Gene Defect in Mdx Myoblast Cultures and Coinjection of these Myoblasts to Mdx Mice with the BMP4 Inhibitor Noggin Dystrophin and utrophin-deficient mice (mdx.utrn$^{-/-}$ mice) were generated by crossing of male mdx$^{+/0}$.utrn$^{-/-}$.hDMD$^{+/-}$ mice female mdx$^{+/+}$.utrn$^{-/-}$.hDMD$^{+/-}$ ('t Hoen et al, manuscript in preparation). Mice were housed under standard laboratory conditions. Animals were fed regular chow and had access to drinking water ad libitum.

Mouse myoblasts were obtained from the isolated hindlimb muscle of male mdx+/o.utrn−/− mice by standard collagenase/dispase treatment and culturing on collagen-coated dishes in standard proliferation medium [22]. Proliferating myoblasts (1×10$^6$ cells/mouse) were transfected with 500 nM of AON-1: GGCCAAACCUCGGCUUACCU (SEC ID No: 9)

(2'-O-methyl phosphorothioate, Eurogentec), complexed with polyethylenimine (Exgen500, MBI Fermentas, 3.5 µl per µg AON). At 2 days after transfection, cells were pelleted and taken up in 7 µl Hank's balanced salt solution, containing or not Noggin, a well-known BMP4 inhibitor (different amounts: 0, 10, 50 or 100 ng). Cells were injected in the tibialis anterior muscle of female mdx+/+.utrn−/− mice with a 50 mm-tip glass pipette. At 3 or 10 days after the injection, mice were sacrificed, and serial cryosections were made. Sections were stained with heamoxylin/eosin and with dystrophin and Y-chromosome-specific antibodies to analyze for cell survival, migration and dystrophin expression.

TABLE 1

Figure 1:
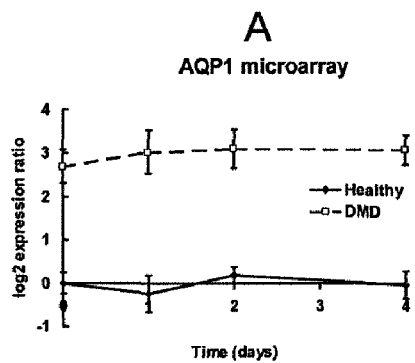
FIG. 1. Gene expression of AQP1 (A) and BMP4 (B) determined with oligonucleotide microarrays (upper panel) or quantitative RT-PCR (lower panel) (Lightcycler, Roche). On the x-axis time is displayed in days. On the y-axis either the log 2 expression ratio (normalized to healthy at t=0) or the −Δ(Ct) (normalized to healthy at t=0) are displayed. The Ct value is proportional to the $^2$ log of the initial amount of mRNA and thus comparable to the $^2$ log expression ratio. Vertical bars represent standard deviations of the different cultures (n=3).
Figure 1:
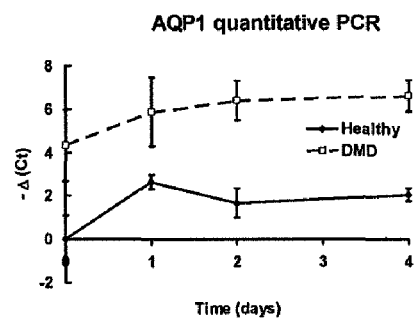
Figure 1:
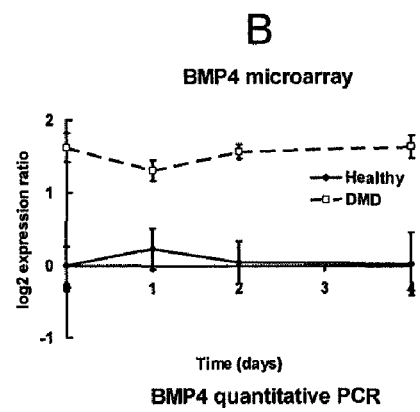
Figure 1:
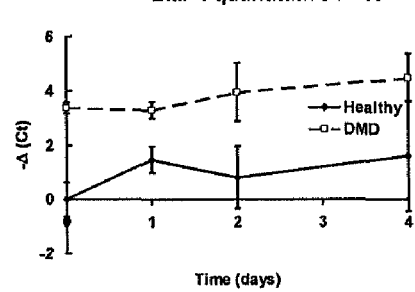
Figure 2:
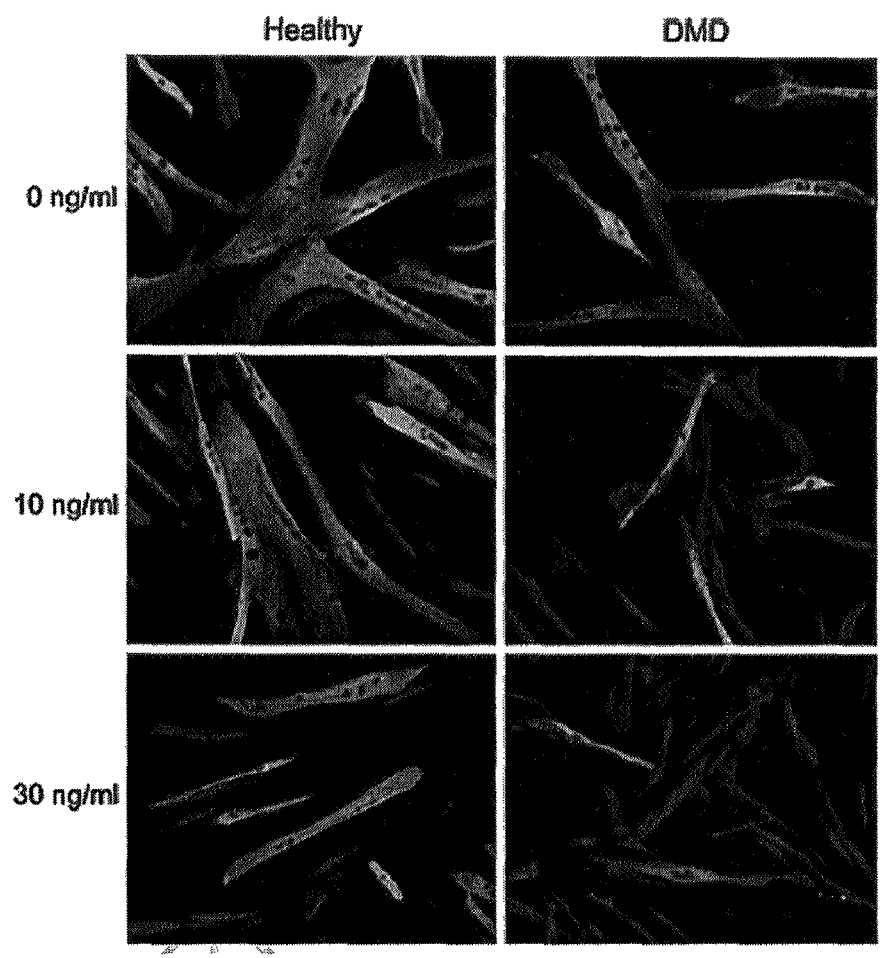
FIG. 2. Immunohistochemical staining of healthy and DMD myotubes incubated with different concentrations of BMP4, evaluated on day 7 of differentiation. Cells were stained with DAPI (blue) and antibodies to desmin (red) and myosin (green).
Figure 3:
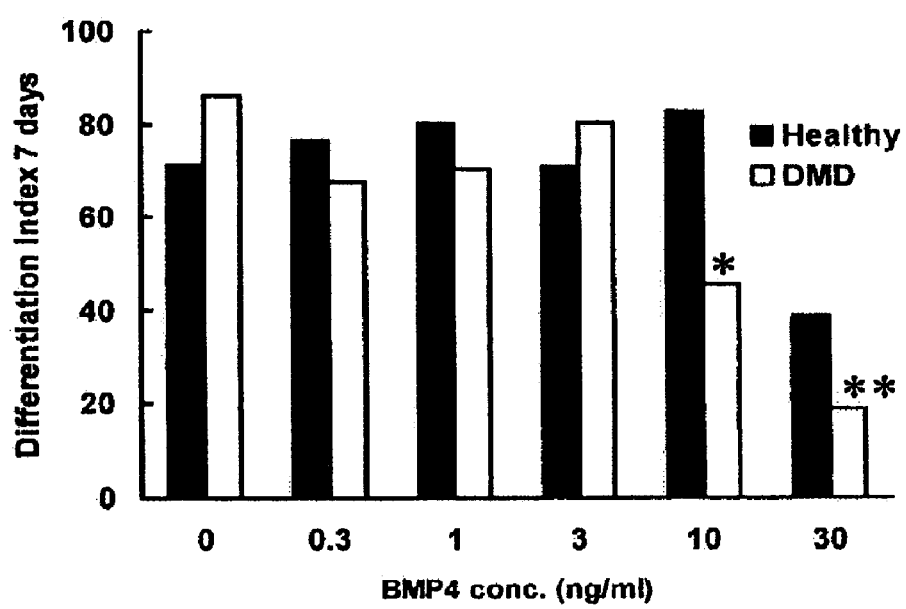
FIG. 3. Differentiation index of healthy and DMD myoblasts after addition of different concentrations of recombinant BMP4. Cells were fixed at day 7. Regression model, **p<0.01, *p<0.05.
Figure 4:
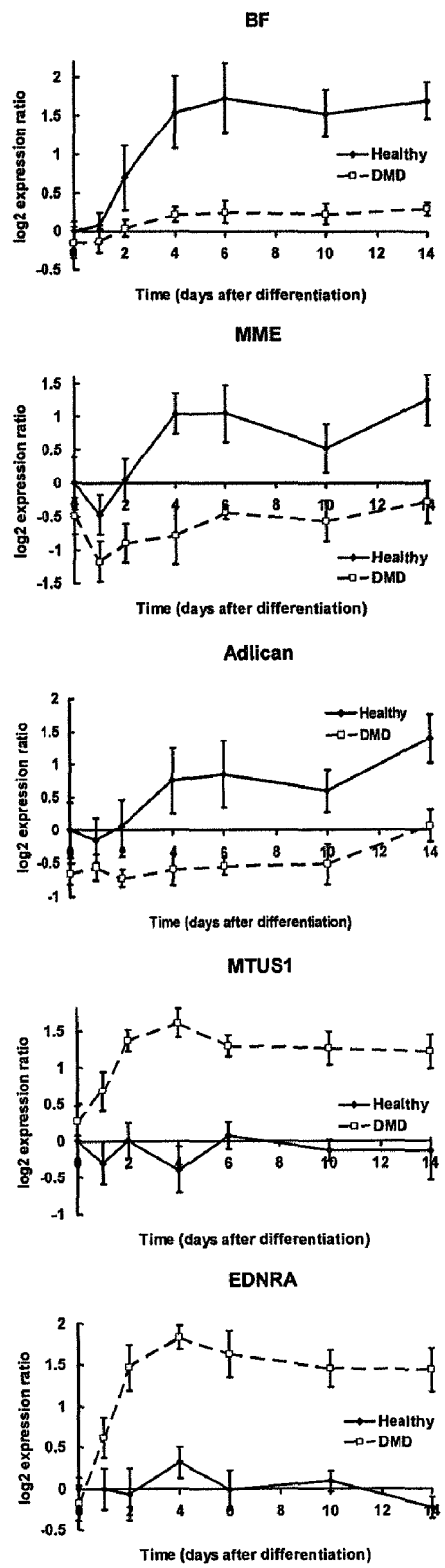
FIG. 4. Log 2 gene expression ratios of genes differentially expressed between healthy and DMD myoblasts after induction of differentiation; BF, MME, Adlican, MTUS1, EDNRA. Vertical bars show standard deviations of the different lines used (n=3).
Figure 5:
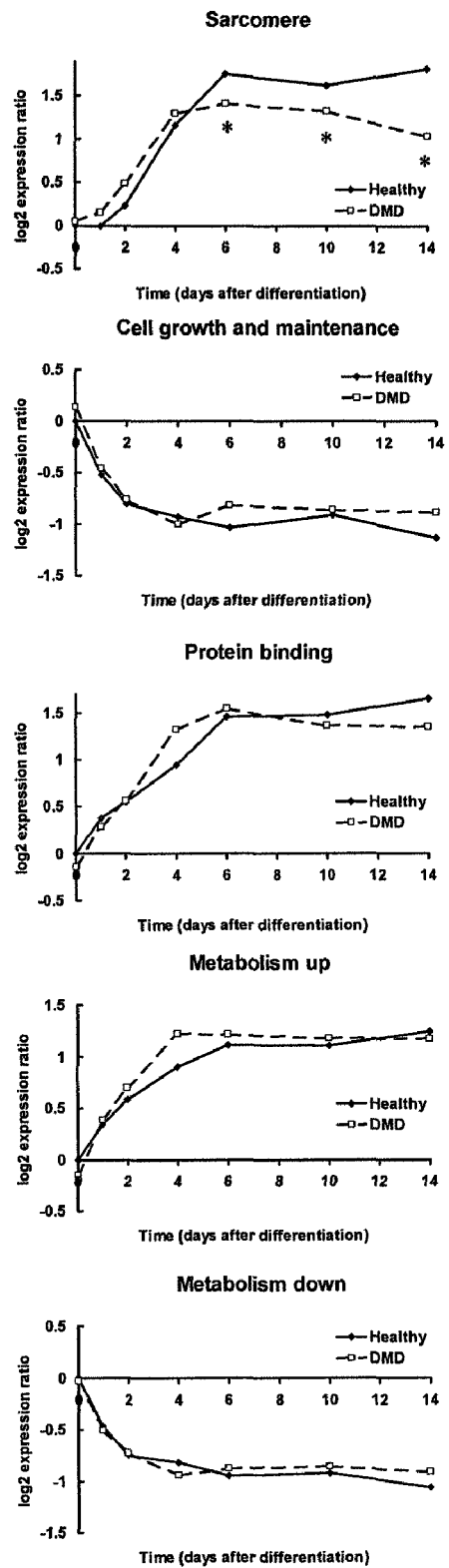
FIG. 5. Mean log 2 gene expression of genes in different functional categories during healthy and DMD myoblast fusion. Sarcomeric genes show in late DMD myogenesis (day 6, 10 and 14) a decrease in gene expression. *Paired t-test, p<0.01. Genes involved in other functional categories (cell growth and maintenance, protein binding, metabolism up and metabolism down) do not show a significant difference between healthy and DMD at any time point (n≧6).
Figure 6:
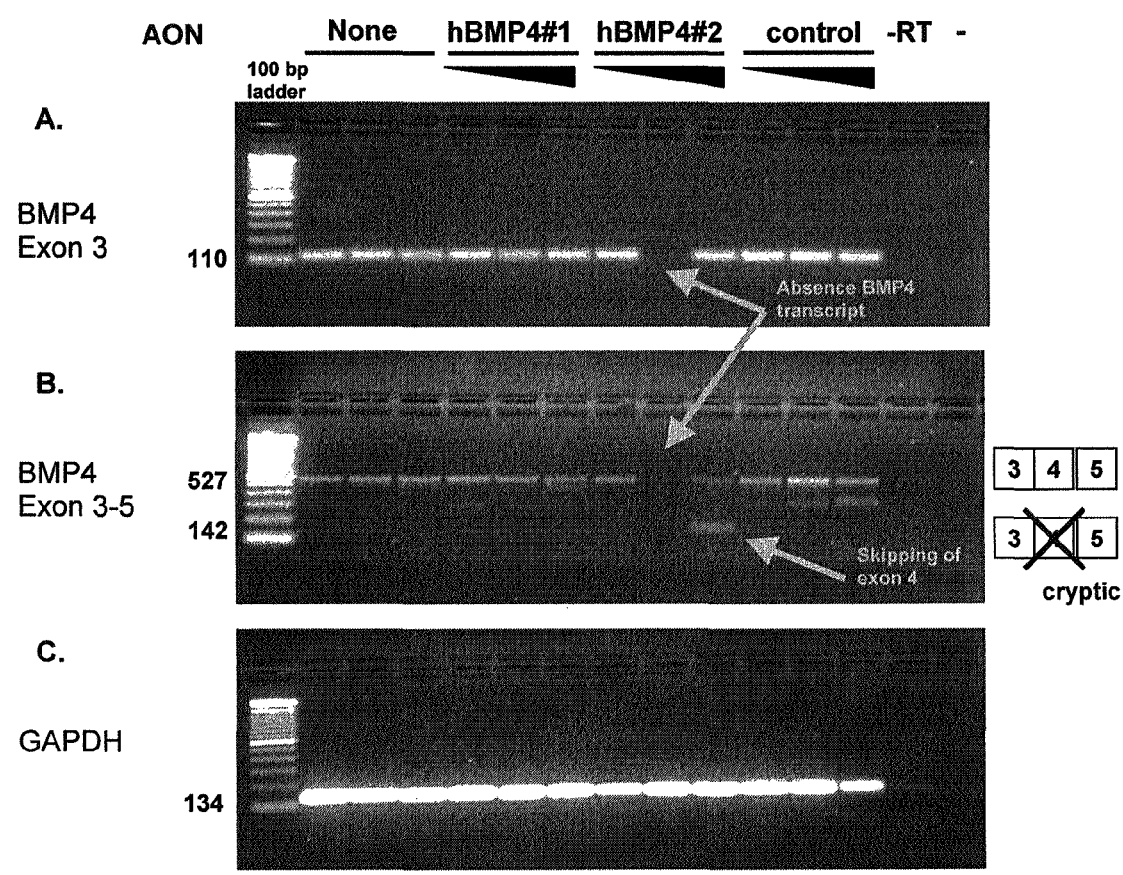
FIG. 6. Ethidium bromide-stained agarose gel demonstrating the antisense oligonucleotide-mediated skipping of exon 4 of human BMP4 in myoblasts of a Duchenne patient (experiment described as example 2). Panel A shows the fragments obtained with PCR 1 (exon 3 of the BMP4 mRNA); panel B shows the fragments obtained with PCR 2 (exon 3-5 of the BMP4 mRNA). The product in which exon 4 is skipped has a size of 142 nucleotides. Panel C shows the fragments obtained with PCR 3 (GAPDH mRNA).
Figure 7:
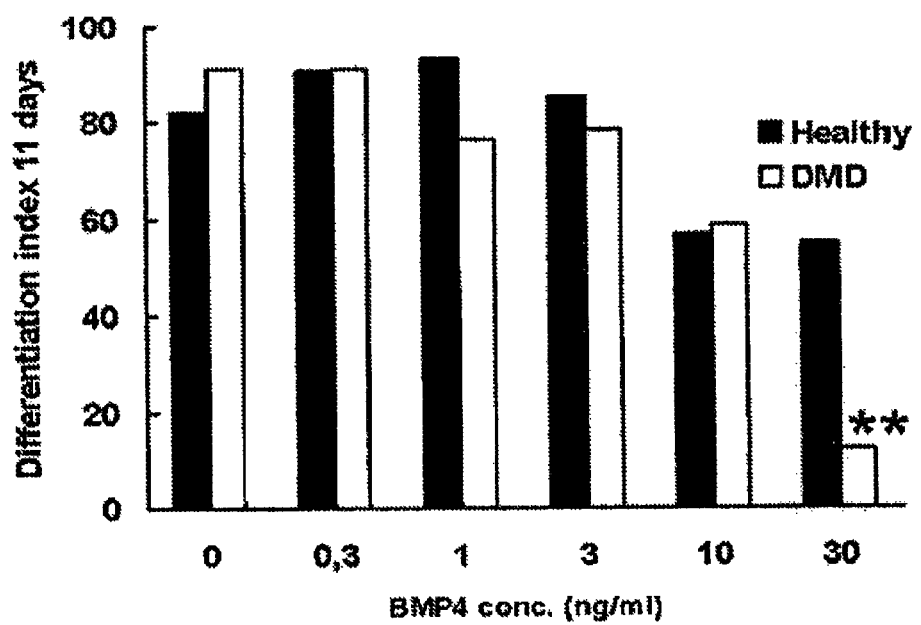
FIG. 7. Differentiation index of healthy and DMD myoblasts after addition of different concentrations of recombinant BMP4. Cells were fixed at day 11. Regression model, *p<0.05.
Figure 8:
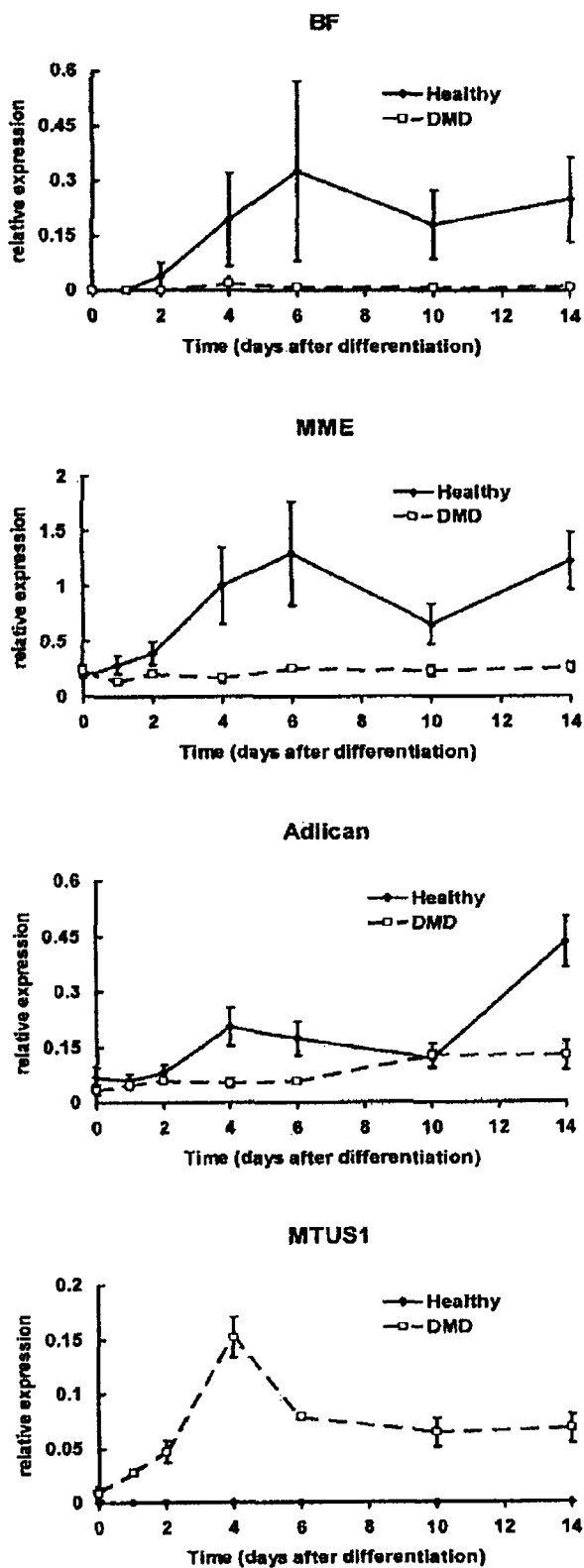
FIG. 8. Gene expression levels of genes differentially expressed in time between healthy and DMD myoblast fusion tested with RT-MLPA; BF, MME, Adlican, MTUS1. Vertical bars show standard error for the different lines used (n=3).

Genes showing differential gene expression
(>2-fold) between healthy and DMD myoblasts

| Genbank | Symbol | Sequence Description | Fold change |
|---|---|---|---|
| H24316 | AQP1 | aquaporin 1 (channel-forming integral protein, 28 kDa) | 6.48 |
| AA463225 | BMP4 | bone morphogenetic protein 4 | 3.08 |
| AA704587 | EST | ESTs, Weakly similar to hypothetical protein FLJ20958 [*Homo sapiens*] [*H. sapiens*] | 2.07 |
| R97066 | TAL1 | T-cell acute lymphocytic leukemia 1 | 2.30 |
| R38539 | FGF2 | fibroblast growth factor 2 (basic) | −2.20 |
| AA598601 | IGFBP3 | insulin-like growth factor binding protein 3 | −2.34 |
| AA664101 | ALDH1A1 | aldehyde dehydrogenase 1 family, member A1 | −2.05 |

TABLE 2

Generalized linear regression model for differentiation index

| Coefficients | P-value |
|---|---|
| Intercept | $4.02 \cdot 10^{-7}$ *** |
| Cell line (DMD) | 0.22844 |
| Concentration BMP4 0.3 ng/ml | 0.47855 |
| Concentration BMP4 1 ng/ml | 0.30271 |
| Concentration BMP4 3 ng/ml | 0.86939 |
| Concentration BMP4 10 ng/ml | 0.48777 |
| Concentration BMP4 30 ng/ml | 0.00867 ** |
| Days in differentiaton (11 days) | 0.09281 |
| Int. cell line - con. BMP4 0.3 ng/ml | 0.25261 |
| Int. cell line - con. BMP4 1 ng/ml | 0.08274 |
| Int. cell line - con. BMP4 3 ng/ml | 0.43757 |
| Int. cell line - con. BMP4 10 ng/ml | 0.04648 * |
| Int. cell line - con. BMP4 30 ng/ml | 0.00756 ** |

Intercept: baseline proportion for the healthy cell culture, with 0.3 ng/ml BMP4 at day 7.
*** $P < 0.001$,
** $P < 0.01$,
* $P < 0.05$

SUPPLEMENTAL TABLE 2

Generalized linear regression model for differentiation index

| Coefficients | P-value |
|---|---|
| Intercept | $4.02 \cdot 10^{-7}$ *** |
| Cell line (DMD) | 0.22844 |
| Concentration BMP4 0.3 ng/ml | 0.47855 |
| Concentration BMP4 1 ng/ml | 0.30271 |
| Concentration BMP4 3 ng/ml | 0.86939 |
| Concentration BMP4 10 ng/ml | 0.48777 |
| Concentration BMP4 30 ng/ml | 0.00867 ** |
| Days in differentiaton (11 days) | 0.09281 |
| Int. cell line - con. BMP4 0.3 ng/ml | 0.25261 |
| Int. cell line - con. BMP4 1 ng/ml | 0.08274 |
| Int. cell line - con. BMP4 3 ng/ml | 0.43757 |
| Int. cell line - con. BMP4 10 ng/ml | 0.04648 * |
| Int. cell line - con. BMP4 30 ng/ml | 0.00756 ** |

Intercept: baseline proportion for the healthy cell culture, with 0.3 ng/ml BMP4 at day 7.
*** $P < 0.001$,
** $P < 0.01$,
* $P < 0.05$

TABLE 3

Generalized linear regression model for differentiation index, ANOVA table

| Variables | P-value |
|---|---|
| Cell line | 0.04069 * |
| Concentration BMP4 | 4.74e−05 *** |
| Days in diffentiation | 0.09281 |
| Int. cell line - concentration | 0.08305 |

*** $P < 0.001$,
** $P < 0.01$,
* $P < 0.05$

SUPPLEMENTAL TABLE 3

Generalized linear regression model for differentiation index, ANOVA table

| Variables | P-value |
|---|---|
| Cell line | 0.04069 * |
| Concentration BMP4 | 4.74e−05 *** |
| Days in diffentiation | 0.09281 |
| Int. cell line - concentration | 0.08305 |

*** $P < 0.001$,
** $P < 0.01$,
* $P < 0.05$

SUPPLEMENTAL TABLE 1a

Genes showing differential gene expression between healthy
and DMD myoblast fusion (Genes upregulated in DMD)

| Genbank | Name | Sequence Description | p-value | Log2 expression difference (DMD-healthy) | | | | | | |
|---|---|---|---|---|---|---|---|---|---|---|
| | | | | 0 | 1 | 2 | 4 | 6 | 10 | 14 |
| H24316 | AQP1 * | aquaporin 1 (channel-forming integral protein, 28kDa)* | 1.11E−16 | 2.70 | 3.27 | 2.92 | 3.12 | 2.44 | 2.80 | 1.99 |

SUPPLEMENTAL TABLE 1a-continued

Genes showing differential gene expression between healthy
and DMD myoblast fusion (Genes upregulated in DMD)

| Genbank | Name | Sequence Description | p-value | Log2 expression difference (DMD-healthy) | | | | | | |
|---|---|---|---|---|---|---|---|---|---|---|
| | | | | 0 | 1 | 2 | 4 | 6 | 10 | 14 |
| AI268273 | MAP3K5 * | mitogen-activated protein kinase kinase kinase 5* | 1.11E−16 | 0.97 | 1.15 | 0.85 | 0.67 | 0.61 | 0.77 | 0.65 |
| L06622 | EDNRA * | endothelin receptor type A* | 1.11E−16 | −0.17 | 0.62 | 1.53 | 1.52 | 1.64 | 1.36 | 1.65 |
| AA463225 | BMP4 * | bone morphogenetic protein 4* | 1.55E−15 | 1.62 | 1.08 | 1.53 | 1.62 | 1.17 | 1.36 | 0.70 |
| AA496896 | MTSG1 * | transcription factor MTSG1* | 1.59E−14 | 0.27 | 0.97 | 1.36 | 2.00 | 1.22 | 1.39 | 1.35 |
| AA448194 | SMN1 * | survival of motor neuron 1, telomeric* | 9.14E−12 | 0.54 | 0.47 | 0.65 | 0.55 | 0.49 | 0.71 | 0.50 |
| AA773333 | DPM2 | dolichyl-phosphate mannosyl-transferase polypeptide 2, regulatory subunit | 3.86E−11 | 0.49 | 0.78 | 0.67 | 0.51 | 0.58 | 0.71 | 0.49 |
| AI359037 | STX3A | Syntaxin 3A | 1.13E−09 | 0.49 | 0.82 | 0.81 | 0.43 | 0.68 | 1.09 | 0.76 |
| AA404269 | PRICKLE1 | Prickle 1-like (*Drosophilla*) | 1.16E−09 | 0.53 | 0.78 | 0.84 | 1.14 | 0.71 | 0.89 | 0.46 |
| AA437212 | AP1S2 | adaptor-related protein complex 1, sigma 2 subunit | 1.81E−09 | 0.32 | 0.55 | 0.80 | 0.62 | 0.98 | 0.75 | 0.69 |
| R44617 | MDFI | MyoD family inhibitor | 1.89E−09 | 0.11 | 0.62 | 0.68 | 1.44 | 0.99 | 1.24 | 0.61 |
| AA456821 | NETO2 | neuropilin (NRP) and tolloid (TLL)-like 2 | 3.86E−09 | 0.84 | 0.71 | 0.60 | 1.00 | 0.93 | 0.86 | 0.96 |
| AI336948 | BACH1 | BTB and CNC homolgy 1, basic leucine zipper transcription factor 1 | 6.46E−09 | 0.59 | 0.77 | 0.71 | 0.65 | 0.64 | 0.79 | 0.63 |
| H42679 | HLA-DMA | major histocompatability complex, class II, DM alpha | 7.65E−09 | 0.93 | 1.19 | 0.92 | 1.02 | 0.49 | 0.60 | 0.56 |
| AA402874 | PLTP | phospholipid transfer protein | 9.83E−09 | 0.17 | 0.42 | 0.55 | 1.47 | 0.98 | 1.29 | 0.59 |
| AA424824 | DSTN * | destrin (actin depolymerizing factor)* | 1.62E−08 | 0.75 | 0.95 | 0.68 | 0.77 | 0.69 | 0.52 | 0.59 |
| AA918646 | KIAA0830 | KIAA0830 protein | 4.74E−08 | 0.73 | 0.87 | 0.95 | 0.27 | 0.28 | 0.46 | 0.20 |
| NM_00426 | FADS2 | fatty acid desaturase 2 | 1.20E−07 | 0.30 | 0.62 | 1.22 | 1.22 | 0.11 | 0.71 | 0.17 |
| N35907 | KIAA0830 | KIAA0830 protein | 2.07E−07 | 0.65 | 0.85 | 0.95 | 0.38 | 0.02 | 0.28 | 0.13 |
| AJ249545 | HEY2 | hairy/enhancer-of-split related with YRPW motif 2 | 3.62E−07 | 0.58 | 0.82 | 0.75 | 1.20 | 0.91 | 0.55 | 0.99 |
| N51002 | PPFIA2 | Protein tyrosine phosphatase, receptor type, f polypeptide (PTPRF), | 3.77E−07 | 0.69 | 0.75 | 0.42 | 0.68 | 0.59 | 0.74 | 0.46 |

SUPPLEMENTAL TABLE 1a-continued

Genes showing differential gene expression between healthy
and DMD myoblast fusion (Genes upregulated in DMD)

| Genbank | Name | Sequence Description | p-value | \multicolumn{7}{c}{Log2 expression difference (DMD-healthy)} | | | | | | |
| --- | --- | --- | --- | --- | --- | --- | --- | --- | --- | --- |
| | | | | 0 | 1 | 2 | 4 | 6 | 10 | 14 |
| | | interacting protein (liprin), alpha 2 | | | | | | | | |
| H74106 | LDB2 | LIM domain binding 2 | 4.64E−07 | 0.29 | 0.39 | 0.82 | 0.82 | 0.80 | 0.59 | 0.61 |
| AA505056 | PAK2 | P21 (CDKN1A)-activated kinase 2 | 5.53E−07 | 0.86 | 0.80 | 0.79 | 0.44 | 0.91 | 0.86 | 0.44 |
| R26417 | STAT5B | Signal transducer and activator of transcription 5B | 6.05E−07 | 0.43 | 0.33 | 0.47 | 0.53 | 0.23 | 0.29 | 0.36 |
| AA449289 | SMTN | smoothelin | 9.74E−07 | 0.40 | 0.63 | 0.71 | 0.71 | 0.16 | 0.75 | 0.36 |
| AI129115 | FLJ10151 | CDNA FLJ10151 fis, clone HEMBA-1003402 | 1.02E−06 | 0.48 | 0.61 | 0.42 | 0.54 | 0.64 | 0.46 | 0.38 |
| AA458981 | FKBP4 | FK506 binding protein 4, 59kDa | 1.03E−06 | 0.66 | 0.43 | 0.43 | 0.73 | 0.34 | 0.81 | 0.48 |
| AF091555 | CTBP1 | C-terminal binding protein 1 | 1.41E−06 | 0.51 | 0.78 | 0.78 | 0.62 | 0.18 | 0.78 | 0.42 |
| AA699926 | SNTA1 * | syntrophin, alpha 1 (dystrophin-associated protein A1, 59kDa, acidic component)* | 1.53E−06 | 0.17 | 0.32 | 0.37 | 0.47 | 0.25 | 0.49 | 0.33 |
| AA677824 | TEAD3 | TEA domain family member 3 | 1.99E−06 | 0.65 | 0.80 | 0.58 | 0.28 | 0.27 | 0.41 | 0.41 |
| H65596 | SAP18 | sin3-associated polypeptide, 18kDa | 2.22E−06 | 0.52 | 0.33 | 0.55 | 0.28 | 0.33 | 0.33 | 0.23 |
| AI291262 | EST | *Homo sapiens*, Similar to diaphanous homolog 3 (*Drosophilla*), clone IMAGE: 5277415, mRNA | 2.94E−06 | 0.79 | 0.51 | 0.76 | 0.59 | 0.93 | 1.06 | 0.59 |
| N63172 | LOC153222 | Retina protein | 3.21E−06 | 0.62 | 0.43 | 0.65 | 0.48 | 0.26 | 0.59 | 0.39 |
| AA282983 | C6orf129 | Chromosome 6 open reading frame 129 | 3.28E−06 | 0.32 | 0.68 | 0.50 | 0.40 | 0.23 | 0.58 | 0.28 |
| AA485871 | MYO1C | myosin IC | 4.11E−06 | 0.51 | 0.95 | 0.39 | 0.66 | 0.02 | 1.14 | 0.66 |
| R97066 | TGM2 | transglutaminase 2 (C polypeptide, protein-glutamine-gamma-glutamyl-transferase) | 4.45E−06 | 1.20 | 1.15 | 0.70 | 0.63 | 0.22 | 0.02 | 0.23 |
| AA464736 | FLJ14525 | hypothetical protein FLJ14525 | 5.40E−06 | 0.24 | 0.77 | 0.63 | 0.21 | 0.31 | 0.71 | 0.45 |
| N70786 | ASH1L | Ash1 (absent, small or homeotic)-like (*Drosophila*) | 5.98E−06 | 0.34 | 0.64 | 0.45 | 0.53 | 0.54 | 0.40 | 0.14 |

SUPPLEMENTAL TABLE 1a-continued

Genes showing differential gene expression between healthy and DMD myoblast fusion (Genes upregulated in DMD)

| Genbank | Name | Sequence Description | p-value | \multicolumn{7}{c}{Log2 expression difference (DMD-healthy)} |
|---|---|---|---|---|---|---|---|---|---|---|
| | | | | 0 | 1 | 2 | 4 | 6 | 10 | 14 |
| AA122049 | FAM35A | Family with sequence similarity 35, member A | 6.60E−06 | 0.15 | 0.46 | 0.53 | 0.33 | 0.41 | 0.48 | 0.42 |
| AF176422 | HEY1 | hairy/enhancer-of-split related with YRPW motif 1 | 7.92E−06 | 0.70 | 0.63 | 1.36 | 0.63 | 0.53 | 0.86 | 1.00 |
| H07920 | MAP2K6 | mitogen-activated protein kinase kinase 6 | 7.96E−06 | 0.13 | 0.21 | 0.28 | 0.22 | 0.38 | 0.34 | 0.59 |
| AA704226 | TNS | tensin | 8.70E−06 | 0.42 | 0.74 | 0.74 | 0.54 | 0.48 | 0.48 | 0.26 |
| L07872 | RBPSUH | recombining binding protein suppressor of hairless (*Drosophilla*) | 9.79E−06 | 0.70 | 0.51 | 0.31 | 0.82 | 0.75 | 0.53 | 0.94 |

* Confirmed by sequencing

SUPPLEMENTAL TABLE 1b

Genes showing differential gene expression between healthy and DMD myoblast fusion (Genes downregulated in DMD)

| Genbank | Name | Sequence Description | p-value | \multicolumn{7}{c}{Log2 expression difference (DMD-healthy)} |
|---|---|---|---|---|---|---|---|---|---|---|
| | | | | 0 | 1 | 2 | 4 | 6 | 10 | 14 |
| R38539 | FGF2 | fibroblast growth factor 2 (basic) | 1.26E−12 | −1.15 | −0.44 | −1.07 | −1.05 | −0.94 | −0.71 | −0.71 |
| AA598601 | IGFBP3 | insulin-like growth factor binding protein 3 | 5.12E−12 | −1.23 | −1.27 | −1.30 | −1.29 | −0.69 | −0.90 | −0.36 |
| H07926 | ACAA2 * | acetyl-Coenzyme A acyltransferase 2 (mitochondrial 3-oxoacyl-Coenzyme A thiolase)* | 1.16E−10 | −0.56 | −0.87 | −0.69 | −0.63 | −0.54 | −0.61 | −0.38 |
| R42685 | IMPA2 * | inositol (myo)-1 (or 4)-monophosphatase 2* | 1.50E−10 | −0.71 | −1.25 | −1.12 | −0.97 | −0.98 | −1.21 | −0.55 |
| R51218 | PIG8 | Translokin | 3.66E−10 | −0.63 | −1.10 | −1.00 | −0.57 | −0.23 | −1.44 | −0.31 |
| AA401441 | BF * | B-factor, properdin* | 6.90E−10 | −0.15 | −0.20 | −0.66 | −1.33 | −1.50 | −1.31 | −1.41 |
| AA669750 | EST | Transcribed locus, weakly similar to NP_689672.2 hypothetical protein MGC45438 | 9.65E−10 | −0.78 | −0.80 | −0.62 | −1.01 | −0.97 | −0.57 | −0.96 |
| J03580 | PTHLH * | parathyroid hormone-like hormone* | 1.43E−09 | −0.44 | −0.91 | −0.83 | −0.72 | −0.61 | −0.77 | −0.42 |
| R98851 | MME * | membrane metalloendopep- | 2.98E−09 | −0.49 | −0.69 | −0.94 | −1.82 | −1.48 | −1.09 | −1.54 |

SUPPLEMENTAL TABLE 1b-continued

Genes showing differential gene expression between healthy
and DMD myoblast fusion (Genes downregulated in DMD)

| Genbank | Name | Sequence Description | p-value | Log2 expression difference (DMD-healthy) | | | | | | |
|---|---|---|---|---|---|---|---|---|---|---|
| | | | | 0 | 1 | 2 | 4 | 6 | 10 | 14 |
| | | tidase, enkephalinase, CALLA, CD10)* | | | | | | | | |
| H23235 | PDGFRA | platelet-derived growth factor receptor, alpha polypeptide | 1.04E−08 | 0.06 | −1.44 | −5.80 | −1.62 | −1.05 | −1.56 | −0.58 |
| AA664101 | ALDH1A1 * | aldehyde dehydrogenase 1 family, member A1* | 2.40E−08 | −1.05 | −1.19 | −1.05 | −0.57 | −0.80 | −1.06 | −1.22 |
| AA630104 | LIPA | lipase A, lysosomal acid, cholesterol asterase (Wolman disease) | 3.87E−08 | −0.84 | −0.36 | −0.18 | −0.59 | −0.66 | −0.45 | −0.49 |
| AA975768 | EMP1 | epithelial membrane protein 1 | 4.61E−08 | −0.75 | −0.37 | −0.71 | −0.79 | −0.63 | −0.50 | −0.56 |
| R59697 | EST | transcribed locus | 7.10E−08 | −0.46 | −0.42 | −0.62 | −0.63 | −0.38 | −0.63 | −0.24 |
| AA464691 | MXRA5 * | matrix-remodelling associated 5* | 1.17E−07 | −0.66 | −0.41 | −0.80 | −1.35 | −1.40 | −1.12 | −1.33 |
| NM_00033 | SGCD | Sarcoglycan, delta (35 kDa dystrophin-associated glycoprotein) | 1.63E−07 | −0.88 | −0.97 | −0.89 | −0.60 | −1.11 | −1.06 | −0.96 |
| AA460353 | MAPKAP1 | Mitogen-activated protein kinase associated protein 1 | 2.02E−07 | −0.36 | −0.52 | −0.39 | −0.30 | −0.69 | −0.43 | −0.83 |
| H14810 | EST | mRNA; cDNa DKFZ-p564CO36 | 2.12E−07 | −0.31 | −0.48 | −0.60 | −0.64 | −0.53 | −0.79 | −0.45 |
| AA190882 | C20orf3 | chromosome 20 open reading frame 3 | 2.59E−07 | −0.51 | −0.61 | −0.56 | −0.29 | −0.77 | −0.55 | −0.57 |
| AA034939 | LAMA2 * | laminin, alpha 2 (merosin, congenital muscular dystrophy)* | 3.97E−07 | −0.74 | −0.68 | −0.79 | −0.70 | −0.64 | −0.42 | −0.43 |
| R61674 | PTP4A1 | protein tyrosine phosphatase type IVA, member 1 | 4.12E−07 | −0.85 | −0.75 | −0.37 | −0.70 | −0.39 | −0.36 | −0.33 |
| W02630 | SDCCAG3 | serological defined colon cancer antigen 3 | 5.94E−07 | 0.05 | −0.24 | −5.91 | −0.51 | −1.25 | −0.13 | −1.82 |
| H18640 | MTX2 | metaxin 2 | 6.09E−07 | −0.37 | −0.26 | −0.37 | −0.67 | −0.55 | −0.69 | −0.42 |
| AA192765 | NDUFA10 | NADH dyhdrogenase (ubiquinone), 1 alpha sub-complex, 10, 42 kDa | 1.02E−06 | −0.67 | −0.30 | −0.42 | −0.15 | −0.29 | −0.57 | −0.25 |
| AA629844 | LRRFIP2 | leucine rich repeat (in | 1.09E−06 | −0.59 | −0.40 | −0.27 | −0.10 | −0.46 | −0.43 | −0.38 |

SUPPLEMENTAL TABLE 1b-continued

Genes showing differential gene expression between healthy and DMD myoblast fusion (Genes downregulated in DMD)

| Genbank | Name | Sequence Description | p-value | Log2 expression difference (DMD-healthy) | | | | | | |
|---|---|---|---|---|---|---|---|---|---|---|
| | | | | 0 | 1 | 2 | 4 | 6 | 10 | 14 |
| | | FLII) interacting protein 2 | | | | | | | | |
| AA456400 | ADSL | adenylosuccinate lyase | 1.45E−06 | −0.52 | −0.62 | −0.39 | −0.27 | −0.74 | −0.64 | −0.60 |
| T62048 | C1S * | complement component 1, s subcomponent* | 1.68E−06 | −0.80 | −0.67 | −0.75 | −0.63 | −0.94 | −0.62 | −0.44 |
| R49329 | C6orf85 | Chromosome 6 open reading frame 85 | 1.78E−06 | −0.43 | −0.75 | −0.52 | −0.32 | −0.62 | −0.65 | −0.43 |
| W55872 | NFKBIA | nuclear factor of kappa light polypeptide gene enhancer in B-cells inhibitor, alpha | 1.84E−06 | −0.16 | −0.32 | −0.59 | −0.71 | −0.99 | −0.63 | −0.48 |
| AA598400 | SFRS3 | splicing factor, arginine/serine-rich 3 | 2.08E−06 | −0.64 | −0.70 | −1.27 | −0.55 | −0.69 | −0.71 | −0.81 |
| R85213 | UBE3A | ubiquitin protein ligase E3A (human papilloma virus E6-associated protein, Angelman syndrome) | 2.34E−06 | −0.57 | −0.78 | −0.63 | −0.49 | −0.69 | −0.65 | −0.41 |
| AA485773 | GRSF1 | G-rich RNA sequence binding factor 1 | 2.55E−06 | −0.64 | −0.39 | −0.25 | −0.28 | −0.51 | −0.42 | −0.52 |
| AA488084 | EST | cDNA clone IMAGE: 4711494, partial cds | 2.60E−06 | −0.42 | −0.87 | −1.72 | −1.52 | −2.60 | −1.05 | −1.16 |
| AA935533 | E2F6 | E2F transcription factor 6 | 2.71E−06 | −0.91 | −1.26 | −0.86 | −0.99 | −1.45 | −1.84 | −0.98 |
| AA939088 | FLJ10781 | hypothetical protein FLJ10781 | 2.74E−06 | −0.89 | −0.23 | −0.28 | −0.43 | −0.22 | −1.25 | −0.82 |
| AA486919 | RPL28 | ribosomal protein L28 | 3.31E−06 | −0.50 | −0.63 | −0.30 | −0.42 | −0.83 | −0.74 | −0.21 |
| AA056395 | HCBP6 | hepatitis C virus core-binding protein 6 | 3.52E−06 | −0.35 | −0.36 | −0.21 | −0.28 | −0.51 | −0.50 | −0.58 |
| W56356 | PEG10 | paternally expressed 10 | 3.59E−06 | −0.15 | −1.26 | −1.92 | −0.34 | −0.64 | −1.71 | 0.17 |
| T72235 | NNMT | nicotinamide N-methyltransferase | 3.77E−06 | −0.58 | −0.43 | −0.57 | −0.15 | −0.71 | −0.50 | −0.49 |
| AI349935 | MYO10 | myosin X | 3.99E−06 | −0.22 | −0.84 | −1.03 | −1.72 | −1.10 | −0.57 | −0.39 |
| AA444051 | S100A10 * | S100 calcium binding protein A10 (annexin II ligand, calpactin 1, light polypeptide (p11))* | 4.10E−06 | −0.67 | −0.80 | −1.32 | −1.31 | −1.00 | −1.21 | −0.84 |

SUPPLEMENTAL TABLE 1b-continued

Genes showing differential gene expression between healthy
and DMD myoblast fusion (Genes downregulated in DMD)

| Genbank | Name | Sequence Description | p-value | Log2 expression difference (DMD-healthy) | | | | | | |
|---|---|---|---|---|---|---|---|---|---|---|
| | | | | 0 | 1 | 2 | 4 | 6 | 10 | 14 |
| H99699 | RPC8 | RNA polymerase III subunit RPC8 | 4.81E−06 | −0.54 | −0.89 | −0.40 | −0.48 | −0.50 | −0.62 | −0.75 |
| AA774755 | SPG3A | spastic paraplegia 3A (autosomal dominant) | 4.82E−06 | −0.18 | −0.40 | −0.50 | −0.22 | −0.75 | −0.86 | −0.38 |
| AA936738 | DFNA5 | deafness, autosomal dominant 5 | 5.25E−06 | −0.59 | −0.08 | −0.27 | −0.30 | −0.57 | −0.29 | −0.23 |
| AA188661 | SH3BP5 | SH3-domain binding protein 5 (BTK-associated) | 5.31E−06 | −0.34 | −0.57 | −0.69 | −0.33 | −0.65 | −0.46 | −0.60 |
| H08424 | HSKM-B | HSKM-B protein | 6.43E−06 | −0.53 | −0.38 | −0.40 | −0.55 | −0.58 | −0.24 | −0.03 |
| AA292054 | GAS1 | growth arrest-specific 1 | 6.62E−06 | −0.21 | −0.34 | −0.70 | −0.87 | −0.77 | −0.71 | −0.60 |
| AA456688 | DRG2 | developmentally regulated GTP binding protein 2 | 6.85E−06 | −0.42 | −0.31 | −0.43 | −0.59 | −0.50 | −0.67 | −0.24 |
| AA496576 | NFE2L1 | nuclear factor (erythroid-derived 2)-like 1 | 7.05E−06 | −0.62 | −0.34 | −0.36 | −0.46 | −0.65 | −0.33 | −0.49 |
| H20908 | ERCC3 | excision repair cross-complementing rodent repair deficiency, complimentation group 3 | 7.95E−06 | −0.37 | −0.36 | −0.43 | −0.16 | −0.56 | −0.57 | −0.25 |
| AA487210 | FLJ10081 | hypothetical protein FLJ10081 | 8.55E−06 | −0.39 | −0.40 | −0.29 | −0.25 | −0.35 | −0.34 | −0.24 |
| W48761 | TAPBP | TAP binding protein (tapasin) | 8.99E−06 | −0.55 | −0.55 | −0.33 | −0.44 | −0.49 | −0.45 | −0.29 |

\* Confirmed by sequencing

The invention claimed is:

1. A method of preparing a medicament for alleviating a symptom of a genetic muscular dystrophy in an individual in need, wherein said medicament comprises an antisense oligonucleotide that causes exon skipping, comprising: providing to a cell of said individual a compound comprising said antisense oligonucleotide;
   comparing the level of expression of BMP4 in said cell before and after providing said compound to said cell to determine whether said compound reduces, inhibits and/or antagonizes expression of Bone Morphogenetic Protein 4 (BMP4) in said cell of said individual;
   wherein a compound that reduces, inhibits and/or antagonizes expression of BMP4 is used to prepare a medicament for alleviating a symptom of a genetic muscular dystrophy; and wherein said medicament is prepared by synthesizing said oligonucleotide and preparing said oligonucleotide for delivery to said individual.

2. The method according to claim 1, wherein said cell is a myoblast cell or precursor thereof.

3. The method according to claim 1, wherein said compound comprises an antisense RNA or a functional equivalent thereof.

4. The method according to claim 1, wherein expression is decreased, inhibited and/or antagonized by means of a virally transduced DNA sequence.

5. The method according to claim 1, wherein said compound is provided to said cell by means of a viral vector.

6. The method according to claim 1, wherein said genetic muscular dystrophy comprises one of the following diseases: Duchenne Muscular Dystrophy (DMD), Becker Muscular Dystrophy (BMD), Congenital Muscular Dystrophy (CMD), Distal Muscular Dystrophy (DD), Emery-Dreifuss Muscular Dystrophy (EDMD), Facioscapulohumeral Muscular Dystrophy (FSH), Limb-Girdle Muscular Dystrophy (LGMD), Myotonic Dystrophy (MMD), Oculopharyngeal Muscular Dystrophy (OPMD).

7. The method according to claim 1, further comprising use of a second compound for the preparation of said medicament, wherein said second compound provides a muscle cell of said individual with at least part of the normal function of a gene that is associated with said genetic muscular dystrophy (mutated gene).

8. The method according to claim 7, wherein said second compound comprises an oligonucleotide, or functional equivalent thereof, for skipping an exon of a dystrophin gene.

9. A method for determining whether a BMP4 anti-sense oligonucleotide or a functional equivalent thereof is capable of inducing skipping of an exon in a BMP4 pre-mRNA containing said exon, said method comprising providing a cell expressing said BMP4 pre-mRNA with said oligonucleotide and determining whether said exon is absent from mature mRNA produced from said pre-mRNA.

10. A method according to claim 9, wherein said anti-sense oligonucleotide or a functional equivalent thereof is complementary to said exon.

11. A method according to claim 9, wherein said anti-sense oligonucleotide or a functional equivalent thereof is complementary to an exon-internal part of said exon.

12. A method according to claim 9, wherein said anti-sense oligonucleotide or a functional equivalent thereof is complementary to exon 4 of BMP4.

13. A method of preparing a medicament for alleviating a symptom of a genetic muscular dystrophy in an individual in need, wherein said medicament comprises an anti-sense oligonucleotide that causes exon skipping or a functional equivalent thereof that is complementary to an exon of BMP-4, said method comprising:
proving to a cell of a-said individual an anti-sense oligonucleotide;
comparing the level of expression of BMP4 in said cell before and after providing said anti-sense oligonucleotide to said cell to determine whether said anti-sense oligonucleotide reduces, inhibits or antagonizes expression of BMP-4 in said cell of said individual;
wherein a compound that reduces, inhibits or antagonizes expression of BMP-4 is used to prepare a medicament for alleviating a symptom of a genetic muscular dystrophy; and wherein said medicament is prepared by synthesizing said oligonucleotide and preparing said oligonucleotide for delivery to said individual.

14. A method according to claim 9, wherein said anti-sense oligonucleotide is provided to said cell by means of a viral vector.

15. A method according to claim 14, wherein said viral vector comprises an expression cassette for expression of said anti-sense oligonucleotide.

16. A method of treating a genetic muscular dystrophy in an individual in need, comprising administering to said individual an anti-sense oligonucleotide that causes exon skipping, or a functional equivalent thereof, that is complementary to an exon of BMP-4, thereby treating said genetic muscular dystrophy.

17. The method of claim 16, wherein said antisense oligonucleotide binds to said exon and decreases the expression of said BMP-4 protein.

* * * * *